United States Patent
Hayano

(10) Patent No.: US 8,269,969 B2
(45) Date of Patent: Sep. 18, 2012

(54) SURFACE INSPECTION DEVICE AND SURFACE INSPECTION METHOD

(75) Inventor: Fuminori Hayano, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/212,930

(22) Filed: Aug. 18, 2011

(65) Prior Publication Data

US 2012/0050739 A1    Mar. 1, 2012

Related U.S. Application Data

(63) Continuation of application No. PCT/JP2010/000954, filed on Feb. 16, 2010.

(30) Foreign Application Priority Data

Feb. 18, 2009 (JP) .................................. 2009-035784

(51) Int. Cl.
    *G01J 4/00*    (2006.01)
(52) U.S. Cl. ....................................................... 356/369
(58) Field of Classification Search .................... 356/369
    See application file for complete search history.

(56) References Cited

U.S. PATENT DOCUMENTS

| | | | |
|---|---|---|---|
| 5,065,034 A | 11/1991 | Kawanami et al. | |
| 6,137,570 A * | 10/2000 | Chuang et al. ............. | 356/237.5 |
| 6,363,167 B1 | 3/2002 | Miyano et al. | |
| 2006/0232769 A1 | 10/2006 | Sugihara et al. | |
| 2009/0147247 A1 | 6/2009 | Endo et al. | |

FOREIGN PATENT DOCUMENTS

| | | |
|---|---|---|
| JP | 64-003545 | 1/1989 |
| JP | 01-217246 | 8/1989 |
| JP | 02-295040 | 12/1990 |
| JP | 03-148049 | 6/1991 |
| JP | 04-74951 | 3/1992 |
| JP | 11-251224 | 9/1999 |
| JP | 2001-267211 | 9/2001 |
| JP | 2005-106754 | 4/2005 |
| JP | 2006-105951 | 4/2006 |
| JP | 2008-96430 | 4/2008 |
| WO | WO 2008/015973 A1 | 2/2008 |

OTHER PUBLICATIONS

International Search Report from the Japanese Patent Office for International Application No. PCT/JP2010/000954, mailing date Apr. 6, 2010.

* cited by examiner

*Primary Examiner* — Roy M Punnoose
(74) *Attorney, Agent, or Firm* — Finnegan, Hederson, Farabow, Garrett & Dunner, L.L.P.

(57) ABSTRACT

There is provided a surface inspection device configured to detect the surface state of the wafer, such as a defect in the uppermost layer and a variation of the CD value, using even diffracted light influenced by the baselayer. The surface inspection device is configured so that an illumination section illuminates the surface of a wafer with a first illuminating light at a high incident angle which is sensitive to a variation of the surface state of the wafer and a second illuminating light at a low incident angle which is insensitive thereto, a detection section detects diffracted light caused by the high and low incident angles, respectively, and a computing unit determines the CD value after correcting the influence of the baselayer of the wafer based on the information relating to the diffracted lights due to the high and low incident angles.

21 Claims, 31 Drawing Sheets

Fig. 29
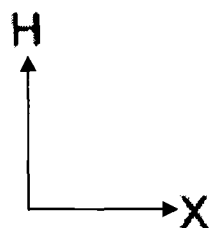
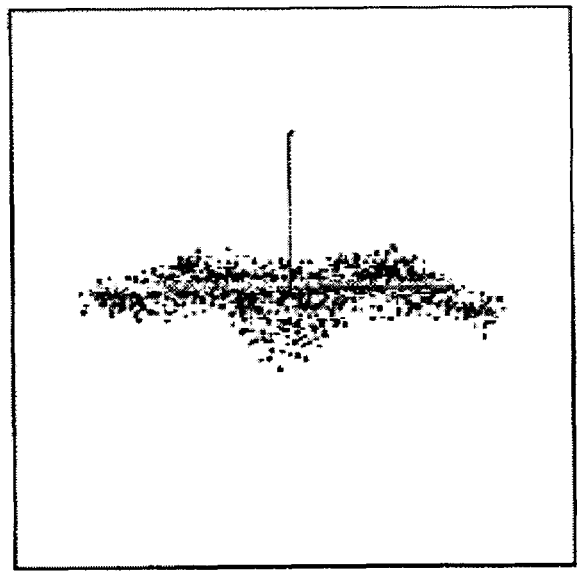
Fig. 30
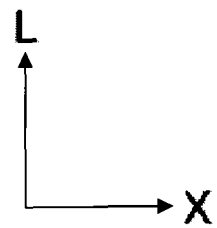
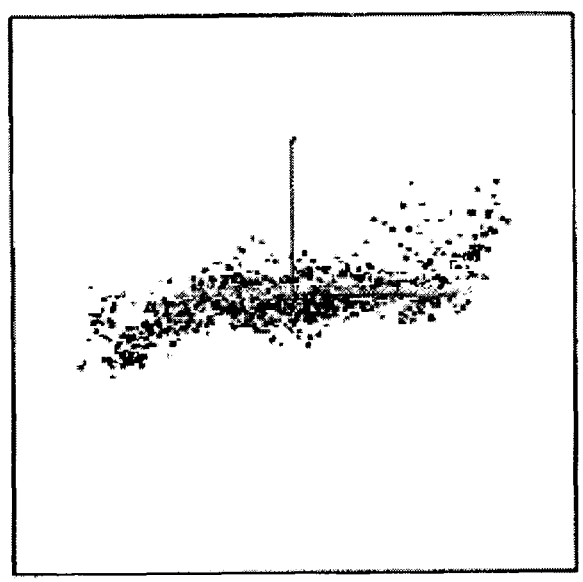

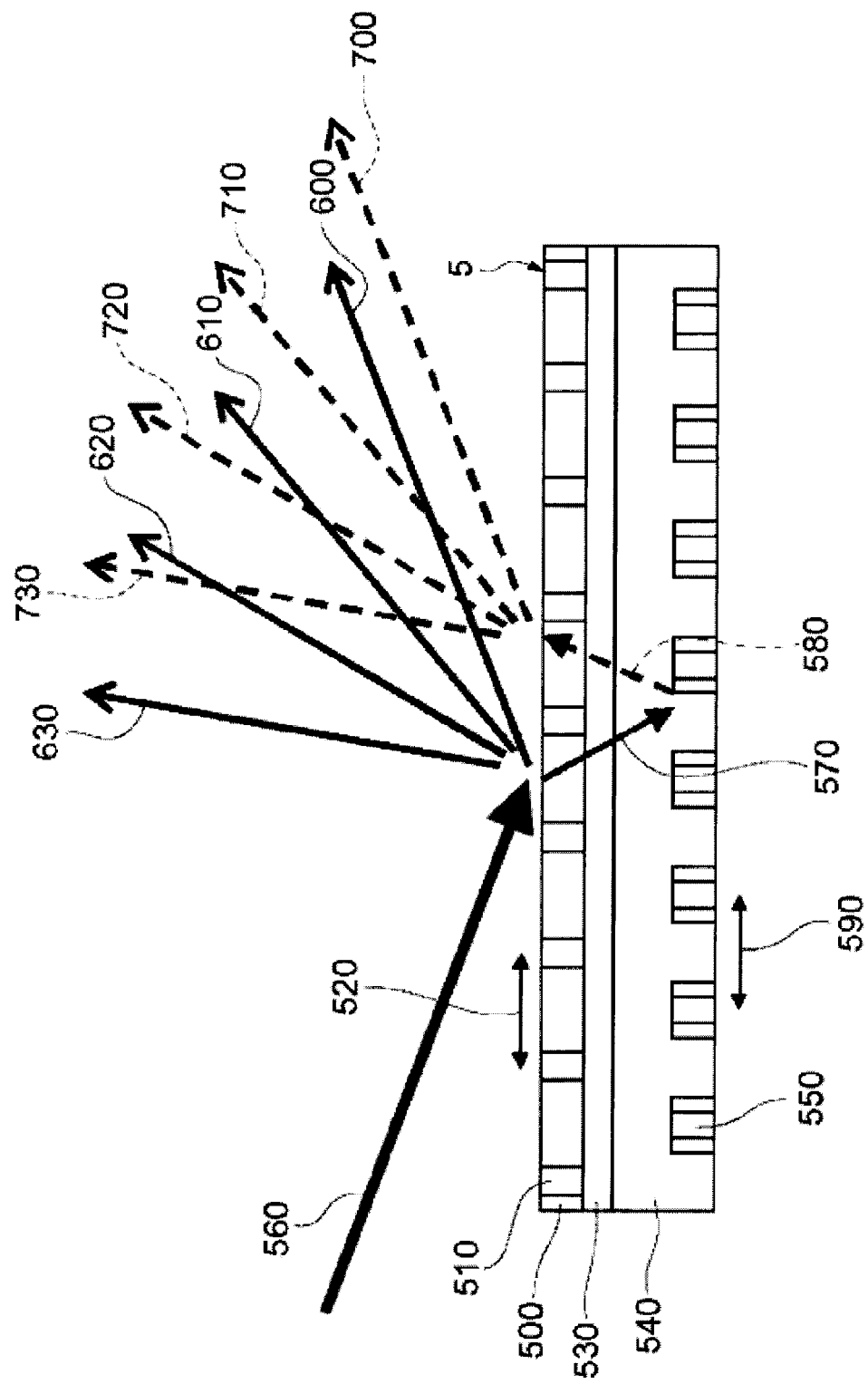

SURFACE INSPECTION DEVICE AND SURFACE INSPECTION METHOD

CROSS REFERENCE TO RELATED APPLICATION

This is a Continuation application of International Application No. PCT/JP2010/000954 filed on Feb. 16, 2010 which claims priority to Japanese patent Application No. 2009-035784 filed on Feb. 18, 2009. The contents of the aforementioned applications are incorporated herein by reference.

BACKGROUND OF THE INVENTION

1. Field of the Invention

The present invention relates to a surface inspection device and method capable of detecting a surface defect in wafer and a CD value variation in line width (or hole diameter) during a semiconductor production process.

2. Description of the Related Art

In recent years, patterns in the semiconductor devices tend to be miniaturized for facilitating the high-speed processing, suppressing the power consumption, and increasing the storage capacity. At the same time, strict managements have also been required for managing the performance of detecting defects occurring in the production process of semiconductor devices, and for managing the line width (to be referred to as "CD" hereinafter; "CD" is the abbreviation for the Critical Dimension). If a surface defect of the wafer or a variation in CD value, which occurs in the exposure process, exceeds an acceptable value, the corresponding wafer or lot is then transferred to a rework process to recover the portion where the problem has occurred, thereby allowing for production of non-defective semiconductor wafers.

For example, when the exposure apparatus has a problem in focal accuracy, an unfavorable change may arise in the cross-sectional shape of the photoresist pattern formed on the wafer surface. Further, with respect to a scanning-type exposure apparatus, diversity in scanning speed may give rise to a fluctuation in exposure amount so as to cause the variation in CD value. As a result, the CD value may go beyond the standard value or a disconnection may be caused after etching. Since the problematic phenomena are compositive, if they cannot be discovered early to solve the problems in time, a large number of lots may become defective, thereby bringing about a great loss.

Therefore, the defect detection and the CD value management performed right after the exposure process are very important. A method for detecting defects is considerably effective for a device for automatically inspecting defects. In this method, an illumination light is irradiated on the semiconductor wafer, the diffracted lights from the repetition pattern on the wafer is received, and the defects are detected based on the fact that the amount of diffracted lights from a defect changes because of the variation in CD value at the defect. The devices adopting the method have been in practical use (see Japanese Patent Application Laid-Open No. 2006-105951, for example). Because such defect inspection devices, which are referred to as macroscopic inspection devices, have a high throughput due to the collective imaging of the entire surface of a wafer, they play a very important role in the production lines. However, in consideration of the property of the devices, there are limitations in the high-resolution inspection for microscopic regions and the quantitative output of the amount of CD value variation.

On the other hand, as a device for managing the CD value, there is an electron microscope device called CD-SEM (Critical-Dimension Scanning Electron Microscope; also called length-measuring SEM). The CD-SEM is configured to measure the line width of line and space (to be referred to as L&S hereinafter), and the diameter of contact holes (to be referred to as C/H hereinafter) or the interval with an adjacent C/H, by using an electron beam, and is configured to output the measurement result as the CD value. Thereby, it is possible to quantitatively determine whether or not the CD value is within the standard. In this manner, although the CD-SEM plays an important role as a measuring apparatus, it is difficult to measure the entire surface of a wafer, because it needs approximately five seconds of time to measure one point. Therefore, under the circumstances, the wafers are measured and managed by the sampling inspection in which one piece of wafer per lot is picked out to perform the inspection for only a few shots within the wafer surface, and for only a few points in each shot.

SUMMARY OF THE INVENTION

In view of this situation of the conventional defect inspection and CD value management, there is a desire for an inspection device which is capable of making quantitative determination at a high speed. It is the influence from base layers (under layers) that comes in the way of facilitating the securing and improving of quantitative performance. This will be explained with reference to FIG. 33. For example, in the case of a hole processing inspection for DRAM, flash memory and the like, an uppermost layer 500 forming the inspection plane (surface) of a semiconductor wafer 5 (to be referred to as a wafer 5 hereinafter) is a photoresist and contact holes 510 are formed with a pitch 520 through an exposure process. An etching resist layer 530 having etching resistance property is provided under the uppermost layer 500 and, by virtue of the etching technique, deep holes with an orderly cross-sectional shape are formed further down to the lower layer. Further, an insulation layer 540 is provided under the etching resist layer 530, and gate wires 550 are provided under the insulation layer 540.

When a light 560 is irradiated on the uppermost layer 500, diffracted lights arise from a contact hole 510. Generally, a diffracted light in a specular direction is referred to as a zeroth-order diffracted light 600. With distance from the zeroth-order diffracted light 600, the diffracted lights are referred to as a first-order diffracted light 610, a second-order diffracted light 620, a third-order diffracted light 630, and so on. An angle between adjacent diffracted lights depends on the wavelength of the light 560 and the pitch 520 of the contact holes 510. The shorter the wavelength of the light 560 is, or the longer the pitch 520 is, the smaller the angle between adjacent diffracted lights becomes. The intensity of each diffracted light is affected not only by the wavelength of the light 560, the transmissivity, absorbability and film thickness of the uppermost layer 500, and the CD value of the contact holes 510, but also by the cross-sectional shape of the contact holes 510, and the like. In the case of the initial exposure process (the element separation process for generating active regions, for example), because there are no base layers, the intensity of the diffracted lights is determined based on the relations as described above. Therefore, when the CD value or cross-sectional shape of the contact holes 510 varies due to problems such as variations in focus, variations in exposure amount and the like in the exposure process, the amount of the diffracted lights varies too. Therefore, it is possible to detect defects based on the amount of change of the diffracted lights.

However, when there are lower layers such as those of FIG. 33, the light 560 partially transmits through the uppermost layer 500 as a transmitted light 570, and reaches a gate wire 550 via the etching resist layer 530 and the insulation layer 540. As a result, another diffracted light 580 also arises from the gate wire 550. When the pitch 590 of the gate wires 550 is identical to the pitch 520 of the contact holes 510, then a zeroth-order diffracted light 700, a first-order diffracted light 710, a second-order diffracted light 720 and a third-order diffracted light 730, which arise from the gate wire 550 and come out of the uppermost layer 500, have the same diffraction angles as those of the zeroth-order diffracted light 600, the first-order diffracted light 610, the second-order diffracted light 620 and the third-order diffracted light 630 which arise from the contact hole 510 of the uppermost layer 500, respectively. Even when the pitch 590 of the gate wires 550 is not identical to the pitch 520 of the contact holes 510, as long as one of the pitch 590 of the gate wires 550 and the pitch 520 of the contact holes 510 is identical to the integral multiple of the other of the pitch 590 and the pitch 520, the diffracted lights 700 to 730 from the gate wire 550 are mixed into the diffracted lights 600 to 630 from the uppermost layer 500, respectively, between the diffracted lights of the orders of integral multiple. Further, when the light 560 has a certain band of the wavelength, depending on the wavelength, it is also possible that the diffracted lights 700 to 730 from the gate wire 550 come to be mixed into the diffracted lights 600 to 630 from the uppermost layer 500, respectively. If the diffracted lights 700 to 730 from the gate wire 550 stayed constant at all times, it would be possible to detect defects of the uppermost layer 500 by simply subtracting the contribution of the diffracted lights 700 to 730. In reality, however, a fluctuation is likely to occur in the influence from the base layers (lower layers).

The baselayer-influence of the base layers varies with each lot, each wafer in a lot, and the place within a wafer surface. This aspect will be explained with reference to FIGS. 34A to 34C. In addition, the same members in each of the diagrams are designated by the same reference numerals.

FIG. 34A shows a case that the gate wires 550 vary in height with the place. After the gate wires 550 are produced, the insulation layer 540 is once formed, and then a CMP process is carried out to uniform the height of the gate wires 550. The CMP process carries out polishing while rotating the wafer along with a polishing pad. At the time, it is possible that the wafer is over-polished on the outer circumferential side such that the height of some gate wires 550 becomes too low. Even if the variation in height does not cause a problem in the process management, because the intensity of diffracted lights is comparatively sensitive to the variation in a height direction, the CD value and cross-sectional shape of the contact holes 510 on the uppermost layer 500 may appear as if they varied in the wafer on the outer circumferential side. Further, the influence varies with different wafers or lots because of the differences in the location of placing the wafer in a state of being polished and the differences in the polishing device.

FIG. 34B shows a case that the etching resist layer 530 becomes nonuniform in thickness due to such as unevenness in creating CVD, temperature control, and the like. When the transmitted light 570 or the diffracted light 580 from the gate wire 550 is transmitted through the etching resist layer 530, it gives rise to an uneven baselayer-influence on the wafer surface, because the amount of the transmitted light or the amount of the absorbed light depends on the film thickness of the etching resist layer 530. Even if it does not bring the uneven baselayer-influence on the wafer surface but is considered uniform, such a difference with respect to each wafer or each lot still becomes a difference of the diffracted lights at the base layer.

FIG. 34C shows a case that a problem in process management has occurred in the stage of producing the gate wires 550 to give rise to a change in the line width of the gate wires per se. Since diffracted lights depend on the pitch and the ratio between the line and the space, the diffracted lights change along with the change of the line width of the gate wires even if the gate wires 550 have the same pitch 590.

Further, in the above explanation, the baselayer-influence is exemplified by the diffracted lights from a gate wire 550. However, in reality, the baselayer-influence comes from not only the diffracted lights from the gate wires 550 but also the diffracted lights from the active region layer further below, the diffracted lights of various pitches and various diffraction orders, and the like. Therefore, it is extremely difficult to specify the origin of the lights and to discuss thereof.

In this manner, with respect to the conventional defect inspection utilizing diffracted lights, there was a limitation in improving inspection accuracy because of receiving the diffracted lights including the baselayer-influence.

In view of such problems, an object of the present invention is to provide a surface inspection device and method capable of correctly detecting the surface condition of a semiconductor substrate such as defects on the uppermost layer, CD value variation, and the like, even when the diffracted lights are under the influence of the base layer.

In order to achieve the above object, according to a first aspect of the present invention, there is provided a surface inspection device including: an illumination section which irradiates illumination lights on a surface of a semiconductor substrate having a plurality of layers;

a detection section which detects diffracted lights from the surface of the semiconductor substrate on which the illumination lights are irradiated; and an inspection section which detects a change of a condition of a pattern on the surface of the semiconductor substrate based on information of the diffracted lights detected by the detection section, wherein the illumination section irradiates, on the surface of the semiconductor substrate, a first illumination light which falls on the surface of the semiconductor substrate at a first incidence angle with respect to a normal of the semiconductor substrate, and a second illumination light which falls on the surface of the semiconductor substrate at a second incidence angle different from the first incidence angle with respect to the normal of the semiconductor substrate;

the detection section detects a first diffracted light caused by the first illumination light irradiated on the surface of the semiconductor substrate, and a second diffracted light caused by the second illumination light irradiated on the surface of the semiconductor substrate; and the inspection section detects the change of the condition of the pattern on the surface to which a correction is made for an influence from layers other than the uppermost layer, based on information of the first diffracted light and the second diffracted light detected by the detection section.

BRIEF DESCRIPTION OF THE DRAWINGS

FIG. 29 is a diagram three-dimensionally showing a relation between the X coordinate on the wafer surface and the diffracted lights due to the high incidence angle in the case of a seventh-order diffracted light due to the high incidence angle;

FIG. 30 is a diagram three-dimensionally showing a relation between the X coordinate on the wafer surface and the diffracted lights due to low incidence angle in the case of a seventh-order diffracted light due to the low incidence angle;

FIG. 33 is a diagram showing an example of diffracted lights diffracted at a wafer surface.

DESCRIPTION OF THE PREFERRED EMBODIMENT

Figure 1:
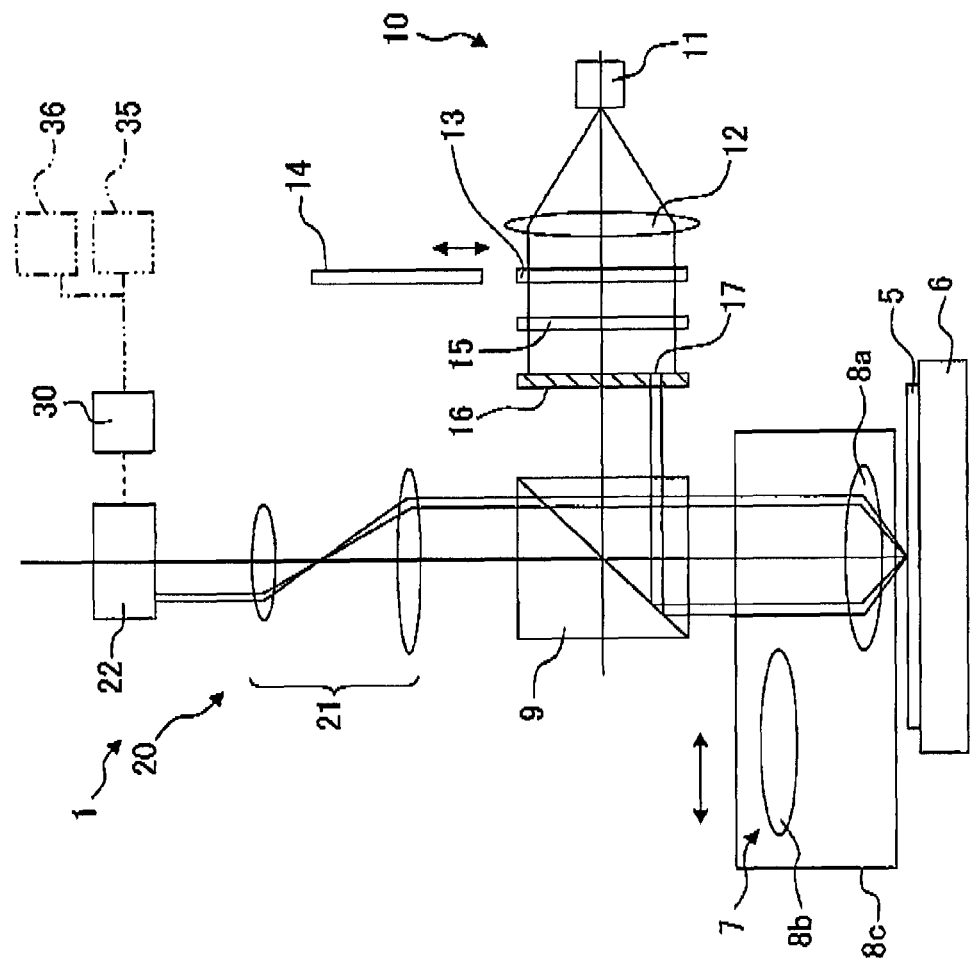
FIG. 1 is a diagram showing an overall configuration of a surface inspection device in accordance with the present invention.

Next, with reference to the accompanying drawings, explanations will be made with respect to a preferred embodiment in accordance with the present invention. FIG. 1 shows a surface inspection device in accordance with the embodiment. This surface inspection device 1 mainly includes a stage 6, an objective lens unit 7, a beam splitter 9, an illumination optical system 10, a detection optical system 20, and a computation processing section 30. A photoresist of a wafer 5 is first exposed by an exposure apparatus (not shown) and developed, then the wafer 5 is conveyed by a conveyance system (not shown) from a wafer cassette or development apparatus (not shown), and finally placed on the stage 6 with the pattern (repetition pattern) formation surface facing upward.

On the surface side of the wafer 5, a plurality of layers are provided as shown in FIG. 33. The plurality of layers include an uppermost layer 500 forming the surface of the wafer 5, a etching resist layer 530 formed on the lower side of the uppermost layer 500, an insulation layer 540 formed on the lower side of the etching resist layer 530, and the like. Further, contact holes 510 are formed on the uppermost layer 500 (a surface of the wafer 5) with a pitch 520 through an exposure process.

The stage 6 holds the wafer 5 placed on the stage 6 by means of vacuum attraction and the like. Further, the stage 6 is configured to be horizontally movable in a longitudinal direction and in a transverse direction along the surface of the wafer 5 and, meanwhile, configured to be rotatable with a normal to the surface of the wafer 5 (an axis in a vertical direction) as the central axis.

The illumination optical system 10 is configured to have a light source 11, a condenser lens 12, a wavelength selection filter 13, a polarizing filter 15, a deformed illumination aperture stop 16 (to be referred to as a deformation aperture stop hereinafter as appropriate) in the arrangement order from the right side to the left side in FIG. 1. A mercury lamp or the like is utilized in the light source 11. The mercury lamp emits lights with a plurality of wavelengths (which may be abbreviated as $\lambda$ hereinafter) such as e-ray ($\lambda$=546 nm), g-ray ($\lambda$=436 nm), h-ray ($\lambda$=405 nm), j-ray ($\lambda$=313 nm) and, furthermore, lights near $\lambda$=250 nm and the like. The wavelength selection filter 13 is utilized to select only a light with a particular wavelength among those lights with multiple wavelengths. Therefore, it is preferable to configure the wavelength selection filter 13 to be capable of selectively switching to change the wavelength or wavelength band for transmission therethrough by means of a switching filter 14 with a different transmission wavelength band.

Further, the light source 11 may be a light source having a broad wavelength band such as a halogen lamp, a blue excitation LED, and the like. In such a case, since the wavelength band of the light of the halogen lamp or the blue excitation LED is broad, the wavelength selection filter 13 may be such a filter as transmits lights of blue, green or red colors therethrough. However, in order to separate diffracted lights of different diffraction orders, each wavelength band is restricted.

The light emitted from the light source 11 is transmitted through the condenser lens 12 and the wavelength selection filter 13, and then transmitted through the polarizing filter 15. The polarizing filter 15 is provided to determine whether the illumination light enters into the wafer 5 in S-polarization or in P-polarization. In the embodiment, the polarizing filter 15 is set so that the illumination light enters into the wafer 5 in S-polarization. Further, the polarizing filter 15 may not be provided on the optical path for realizing non-polarized incidence lights. Further, descriptions will be made hereinafter with respect to what kind of difference there is between S-polarization and P-polarization, and which is more preferable.

The light transmitted through the polarizing filter 15 is transmitted through an aperture 17 of the deformation aperture stop 16 which will be described in detail hereinafter, reflected by the beam splitter 9 in a direction toward the wafer 5 (downward). Then, in the case as shown in FIG. 1, the reflected light is transmitted through a high NA objective lens 8a of the objective lens unit 7, and falls on the surface of the wafer 5 at a comparatively large incidence angle by virtue of a high NA (numerical aperture), where an incidence angle is defined optically as the angle of an incident light with respect to a normal of the wafer 5. The objective lens unit 7 is configured to have the high NA objective lens 8a set such that a comparatively high NA (numerical aperture) is obtainable, a low NA objective lens 8b set such that a low NA (numerical aperture) is obtainable in comparison with the high NA objective lens 8a, and a switching mechanism 8c for inserting one of the high NA objective lens 8a and the low NA objective lens 8b in the optical path between the beam splitter 9 and the wafer 5.

Figure 2:
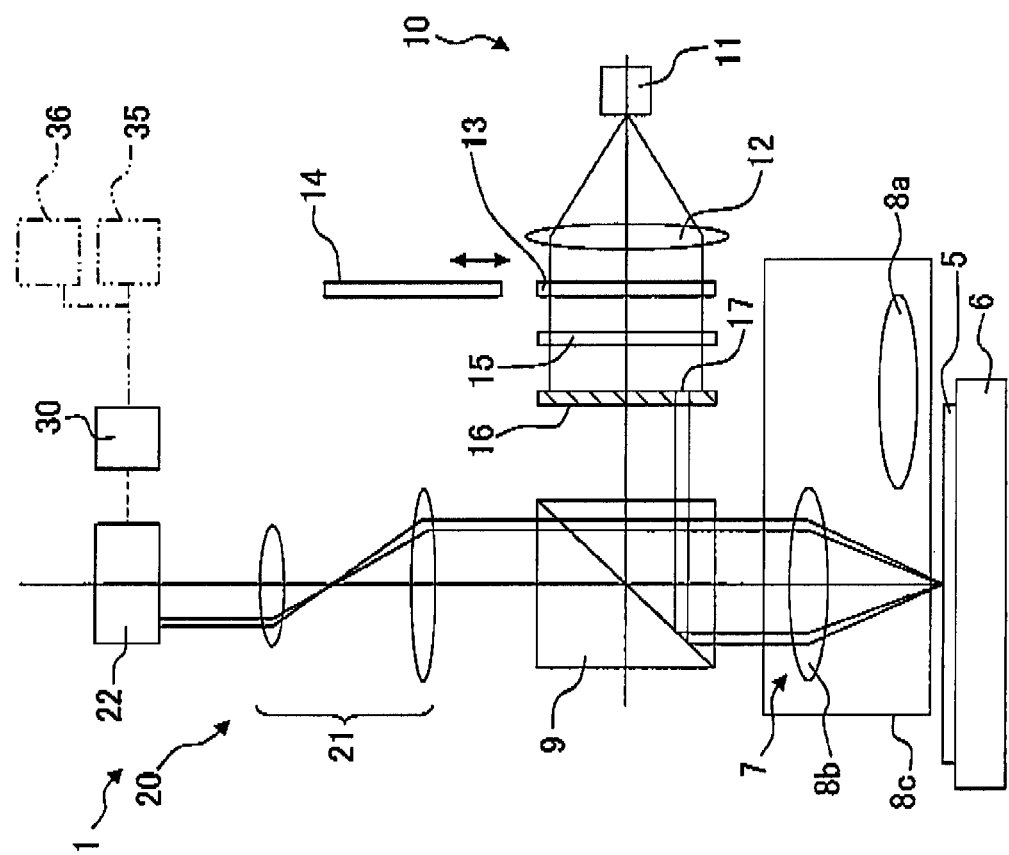
FIG. 2 is a diagram showing the surface inspection device with switched objective lenses.

As shown in FIG. 1, when the switching mechanism 8c inserts the high NA objective lens 8a in the optical path, as described hereinabove, the illumination light reflected by the beam splitter 9 and transmitted through the high NA objective lens 8a (to be referred to as a first illumination light hereinafter) falls on the surface of the wafer 5 at a comparatively large first incidence angle. On the other hand, as shown in FIG. 2, when the switching mechanism 8c inserts the low NA objective lens 8b in the optical path, the illumination light reflected by the beam splitter 9 and transmitted through the low NA objective lens 8b (to be referred to as a second illumination light hereinafter) falls on the surface of the wafer 5 at a second incidence angle that is smaller than the aforementioned first incidence angle, by virtue of a low NA. FIG. 2 shows a state in which the low NA objective lens 8b is inserted in the optical path. Further, the objective lens unit 7 may be a so-called revolver-type rotary interchange mechanism of objective lenses. Further, the incident direction of the illumination light is substantially parallel to the direction of the pattern repetition on the wafer 5.

The detection optical system 20 is configured to have a relay lens 21 and an imaging element 22 such as a two-dimensional CCD and the like. As shown in FIG. 1, when the first illumination light is irradiated on the surface of the wafer 5, the reflected light or diffracted light reflected/diffracted by the wafer 5 is transmitted through the high NA objective lens 8a and the beam splitter 9. Then the optical path length is extended by the relay lens 21, and at the same time the image of the light is expanded (or shrunk) by the relay lens 21. Then, the light comes into the imaging element 22. On the other hand, as shown in FIG. 2, when the second illumination light is irradiated on the surface of the wafer 5, the reflected light or diffracted light reflected/diffracted by the wafer 5 is transmitted through the low NA objective lens 8b and the beam splitter 9. Then the optical path length is extended by the relay lens 21 and at the same time the image of the light is expanded (or shrunk) by the relay lens 21. Then, the light comes into the imaging element 22. The imaging element 22 is provided on the pupil plane of the detection optical system 20. The imaging element 22 photoelectrically converts the reflected light or diffracted light incident on the pupil plane from the wafer 5 into an electrical signal, and outputs a detection signal to the computation processing section 30. Further, when a color CCD is utilized in the imaging element 22 for outputting the red (R), green (G) and blue (B) signals, respectively, then it is possible to leave out the wavelength selection filter 13.

Figure 3:
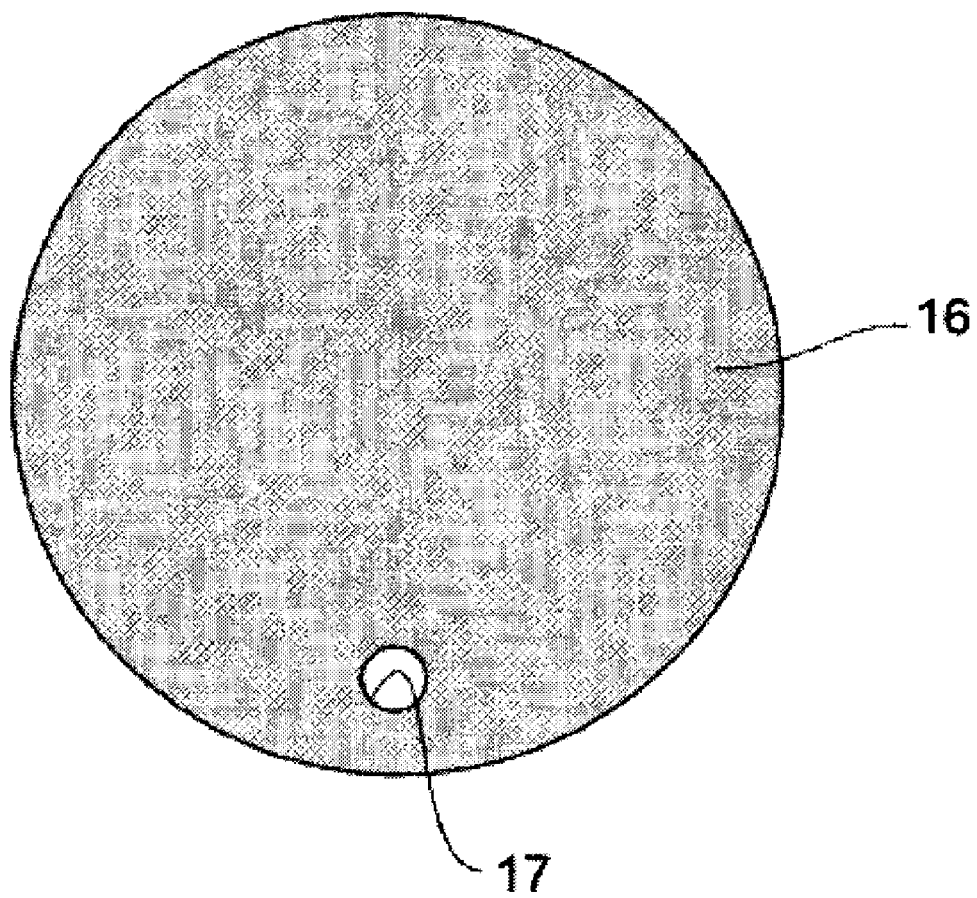
FIG. 3 is a diagram showing a deformation aperture stop.

Hereinbelow, the deformation aperture stop 16 and its function will be explained with reference to FIGS. 3, 4A, and 4B. FIG. 3 shows the deformation aperture stop 16 viewed from a direction of the optical axis. The deformation aperture stop 16 is formed in a disk shape, and the optical axis runs through the center of the deformation aperture stop 16. The circular aperture 17 is provided in the deformation aperture stop 16 at an eccentric position that is eccentric with respect to the optical axis. By virtue of this, the light off the optical axis is allowed to fall on the wafer 5. The incidence angles are different between the cases of the high NA objective lens 8a and the low NA objective lens 8b. In this embodiment, the full aperture (the maximum effective aperture of an objective lens per se) of the high NA objective lens 8a is approximately NA=0.9. Thereby, the incidence angle (the first incidence angle) of the incident light via the aperture 17 of the deformation aperture stop 16 is approximately NA=0.7 to 0.8 (the first incidence angle $\theta 1$=60 degrees or so).

This incidence angle is close to a Brewster's angle calculated from the refractive index of the photoresist. At a Brewster's angle, the P-polarized incident light is transmitted through the uppermost layer 500 almost without being reflected by the uppermost layer 500. On the other hand, the S-polarized incident light has both transmission and reflection components. Since the intensity of diffracted lights depends on the refractive index, considering the diffracted lights from the uppermost layer 500 and the diffracted lights from lower layers such as the gate wires 550, the P-polarized incident light is easy to be affected by the diffracted lights from lower layers in comparison with the S-polarized incident light. In fact, intense diffracted lights from lower layers are observed for the P-polarized incident light in comparison with the S-polarized incident light. Therefore, by setting the polarizing filter 15 (polarizer) so that the S-polarized light component becomes dominant so as to reduce the intensity of the diffracted lights from lower layers, it is possible to obtain the diffracted lights including relatively more information regarding the surface condition changes of the uppermost layer 500 (information regarding variations in the pattern profile and CD value of the contact holes 510 due to focal error, error in exposure amount and abnormality in image plane in the exposure process). However, it is not possible to reduce the diffracted lights from base layers to zero.

Figure 4A:
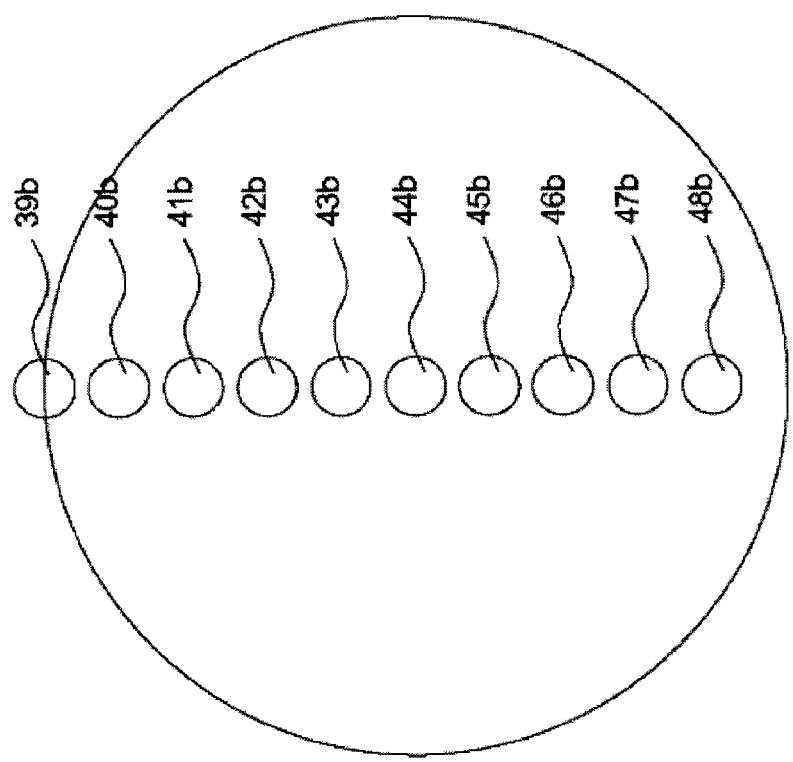
FIGS. 4A and 4B are diagrams showing an example of diffracted lights on a pupil plane.

FIG. 4A shows a pupil image detected by the imaging element 22 utilizing the high NA objective lens 8a. In FIG. 4A, the first-order diffracted light 41a to the eighth-order diffracted light 48a are shown according to the diffraction orders with respect to the zeroth-order diffracted light 40a. Further, the negative first-order diffracted light 39a is present outside the zeroth-order diffracted light 40a. Since the diffracted lights shown in FIG. 4A are those via the high NA objective lens 8a, these diffracted lights will be collectively referred to as a diffracted light H due to high incidence angle in the following explanations. The diffracted lights caused by the light of a large incidence angle (the first incidence angle) will be designated by a reference numeral according to the diffraction order, and will be referred to as diffracted lights H1 (a first-order diffracted light), H2 (a second-order diffracted light) and the like due to high incidence angle. Further, since the sign of the diffracted lights (positive and negative) is defined for the descriptive purpose in the embodiment, the validity of the definition of the sign in terms of optics shall not be inquired herein.

Figure 4B:
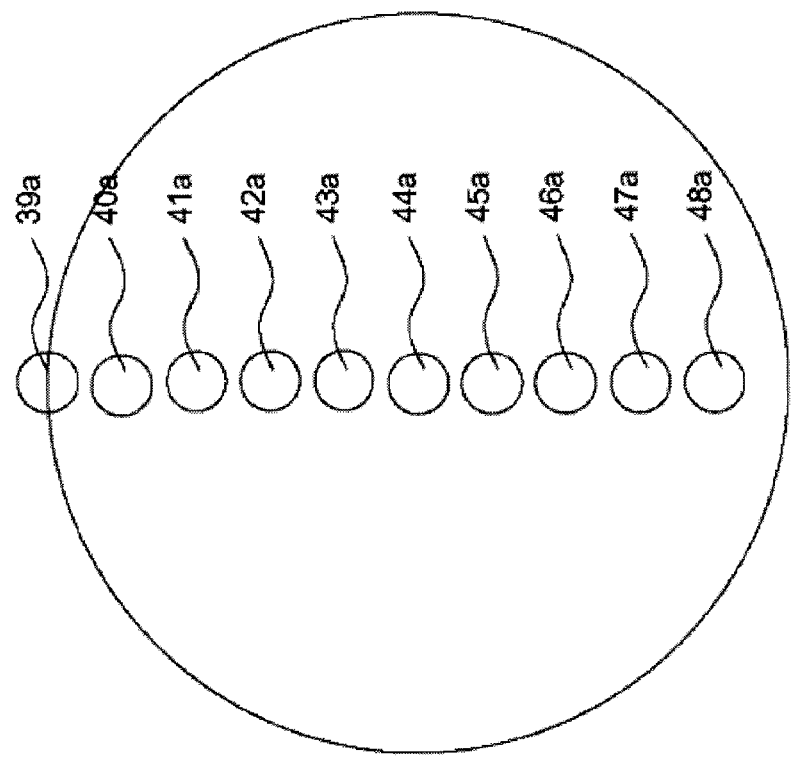

FIG. 4B shows a pupil image detected by the imaging element 22 utilizing the low NA objective lens 8b. In FIG. 4B, the first-order diffracted light 41b to the eighth-order diffracted light 48b, and the negative first-order diffracted light 39b are shown according to the diffraction orders with respect to the zeroth-order diffracted light 40b. Since the low NA objective lens 8b causes a small incidence angle of the light transmitted through the aperture 17 of the deformation aperture stop 16 (closer to a vertical incidence), the diffracted lights differ in condition from the diffracted lights via the high NA objective lens 8a. At the incidence angle due to the low NA objective lens 8b, the S-polarized light has a low refractive index in comparison with the incidence angle to be close to a Brewster's angle when utilizing the high NA objective lens 8a, resulting in a high transmissivity. Therefore, the light reaching down to the base layers increases in amount to cause a greater baselayer-influence on the present case of utilizing the low NA objective lens 8b than the case of utilizing the high NA objective lens 8a. The diffracted lights due to low incidence angle from the low NA objective lens 8b are collectively referred to as a diffracted light L due to low incidence angle in the following explanations. The diffracted lights caused by the light of a small incidence angle (the second incidence angle) will be designated by a reference numeral according to the diffraction orders and will be referred to as diffracted lights L1 (a first-order diffracted light), L2 (a second-order diffracted light) and the like due to low incidence angle.

Therefore, by comparing between FIG. 4A and FIG. 4B, it is suggested that it is possible to eliminate the baselayer-influence by subtracting (by correcting) the information of the diffracted lights via the low NA objective lens 8b from the information of the diffracted lights via the high NA objective lens 8a, because the diffracted lights via the low NA objective lens 8b include more baselayer diffracted lights, and the diffracted lights via the high NA objective lens 8a include the uppermost-layer diffracted lights and the baselayer diffracted lights. Further, when a 100-power objective lens and a 50-power objective lens are used as the high NA objective lens and the low NA objective lens, respectively, the observation region of the 100-power objective lens is φ140 μm, and that of the 50-power objective lens is φ280 μm. Although the observation regions differ in this manner, no problem will occur because the low NA observation region covers the high NA observation region, and the lower-layer variation can be regarded as almost constant within these ranges.

Figure 10:
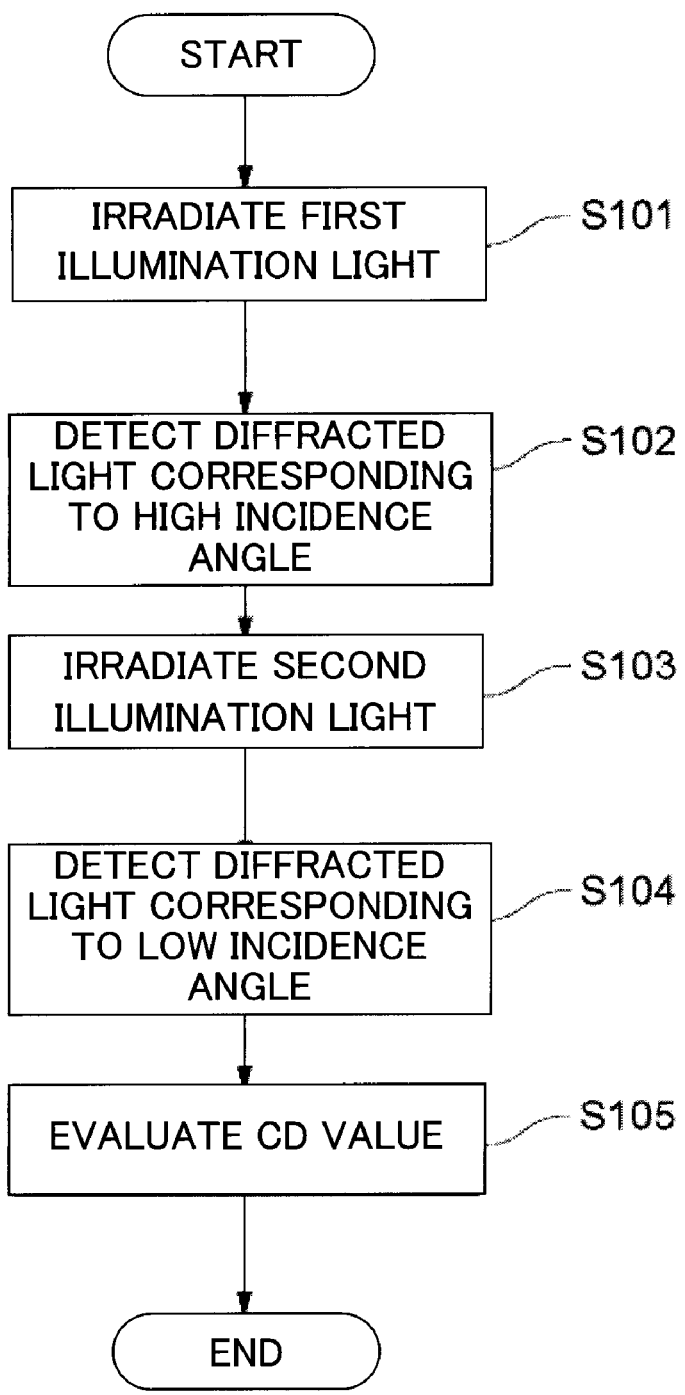
FIG. 10 is a flowchart showing a surface inspection method in accordance with the present invention.

With reference to the flowchart as shown in FIG. 10, explanations will be made with respect to a surface inspection method utilizing the surface inspection device 1 configured as described above. First, an illumination light is irradiated on the surface of the wafer 5 (Step S101). In this case, when the high NA objective lens 8a is used, then the first illumination light is irradiated from the high NA objective lens 8a on the surface of the wafer 5 at a high incidence angle.

Then the diffracted light H due to high incidence angle diffracted at the wafer 5 is transmitted through the high NA objective lens 8a, the beam splitter 9 and the relay lens 21, and the pupil image of the diffracted light H comes into the imaging element 22. Then, the imaging element 22 detects the diffracted light H due to high incidence angle and outputs the detection result to the computation processing section 30 (Step S102).

Next, another illumination light is irradiated on the surface of the wafer 5 (Step S103). Then the switching mechanism 8c switches the lenses from the high NA objective lens 8a to the low NA objective lens 8b, and thus the second illumination light is irradiated from the low NA objective lens 8b on the surface of the wafer 5 at a low incidence angle.

In this case, the diffracted light L due to low incidence angle diffracted by the wafer 5 is transmitted through the low NA objective lens 8b, the beam splitter 9 and the relay lens 21, and the pupil image of the diffracted light L comes into the imaging element 22. Then, the imaging element 22 detects the diffracted light L due to low incidence angle and outputs the detection result to the computation processing section 30 (Step S104).

Then, the computation processing section 30 finds the CD value which has corrected and eliminated the influence from the base layers below the uppermost layer 500 by a method which will be described hereinafter based on the information (brightness values) of the diffracted light H due to high incidence angle and the diffracted light L due to low incidence angle (Step S105). Note that, the sequence may be reversed for detecting the diffracted light H due to high incidence angle and the diffracted light L due to low incidence angle.

Figure 5:
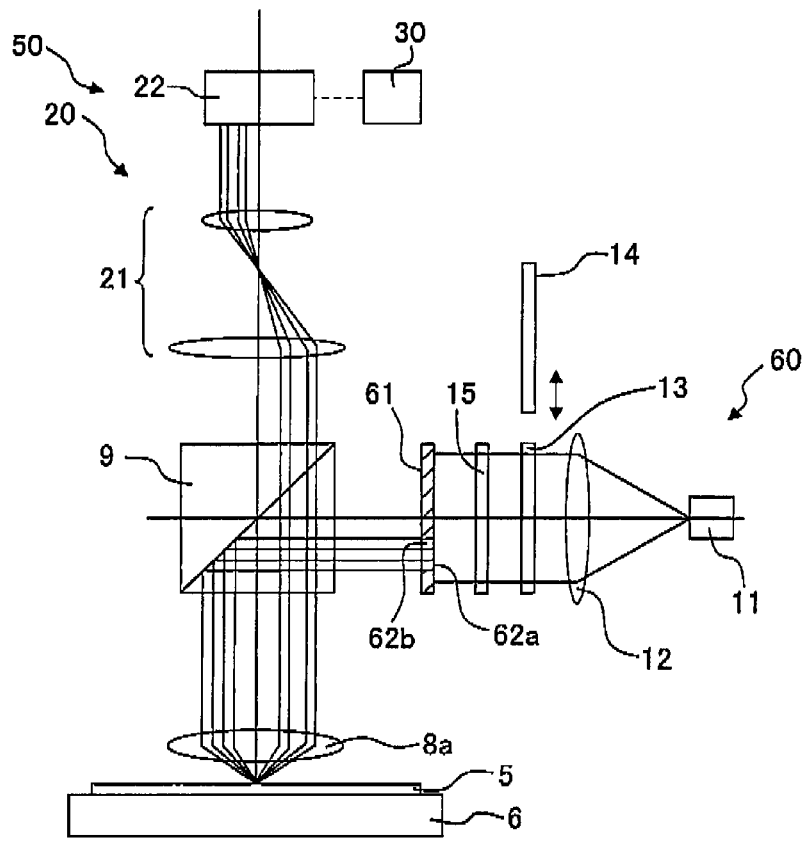
FIG. 5 is a diagram showing a modification of the surface inspection device.

Hereinafter, a modification of the surface inspection device will be explained. FIG. 5 is a configuration diagram showing a surface inspection device 50 in accordance with the modification, wherein the same members as those in FIG. 1 are designated by the same reference numerals. The surface inspection device 50 in accordance with the modification mainly includes a stage 6, a high NA objective lens 8a (100-power lens; NA is approximately 0.9), a beam splitter 9, an illumination optical system 60, a detection optical system 20, and a computation processing section 30. The illumination optical system 60 is configured to have a light source 11, a condenser lens 12, a wavelength selection filter 13, a polarizing filter 15 and a deformation illumination aperture stop 61 (to be abbreviated as a deformation aperture stop hereinafter as appropriate), and these elements are arranged in this order from the right side to the left side in FIG. 5. The light emitted from the light source 11 is transmitted through the condenser lens 12, the wavelength selection filter 13 and the polarizing filter 15, and passes through a first aperture 62a and a second aperture 62b of the deformation aperture stop 61 which will be described in detail hereinafter. Then the light is refracted by the beam splitter 9 in a direction toward the wafer 5 (downward), transmitted then through the high NA objective lens 8a, and finally falls on the surface of the wafer 5.

Figure 6:
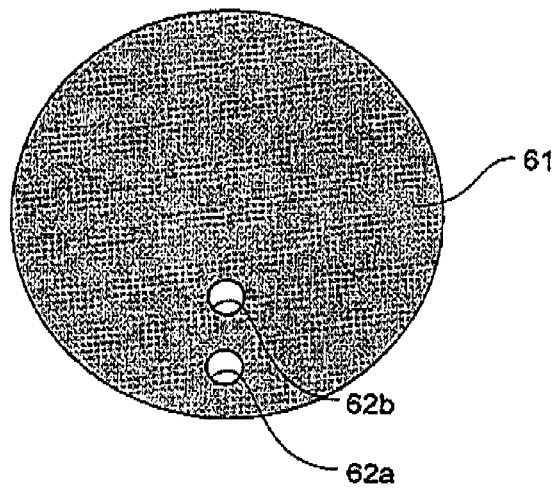
FIG. 6 is a diagram showing a modification of the deformation aperture stop.

The first aperture 62a and the second aperture 62b are formed in the deformation aperture stop 61 which is formed in a disk shape. Further, the first aperture 62a and the second aperture 62b in accordance with the modification are provided both at a size of approximately 100 μm in diameter. Since the deformation aperture stop 61 is approximately 4 mm in diameter, the diffracted lights which are obtained by being transmitted through the apertures 100 μm in diameter and by entering on the wafer can be separated according to the diffraction order. FIG. 6 shows the deformation aperture stop 61 viewed from a direction of the optical axis thereof. The distance from the optical axis to the first aperture 62a in the deformation aperture stop 61 is identical to the distance from the optical axis to the aperture 17 in the deformation aperture stop 16 as shown in FIG. 3. Further, in this configuration, only the high NA objective lens 8a is provided as an objective lens. As a result, the illumination light passing through the first aperture 62a of the deformation aperture stop 61 falls on the surface of the wafer 5 at the same incidence angle as that in the case of utilizing the high NA objective lens 8a with the configuration of FIG. 1. Further, the distance from the optical axis to the second aperture 62b in the deformation aperture stop 61 is provided so that the incidence angle becomes same as that obtained by the low NA objective lens 8b with the configuration of FIG. 1 (the case of FIG. 2). As a result, the incidence angles of the illumination lights obtained via the first aperture 62a and the second aperture 62b are equivalent to those obtained by the configurations of FIGS. 1 and 2, respectively. In this manner, since the two apertures 62a and 62b are formed in the deformation aperture stop 61, it is possible to detect the diffracted light H due to high incidence angle and the diffracted light L due to low incidence angle simultaneously and, furthermore, it is possible to simplify the configuration of the objective lens.

Figure 7:
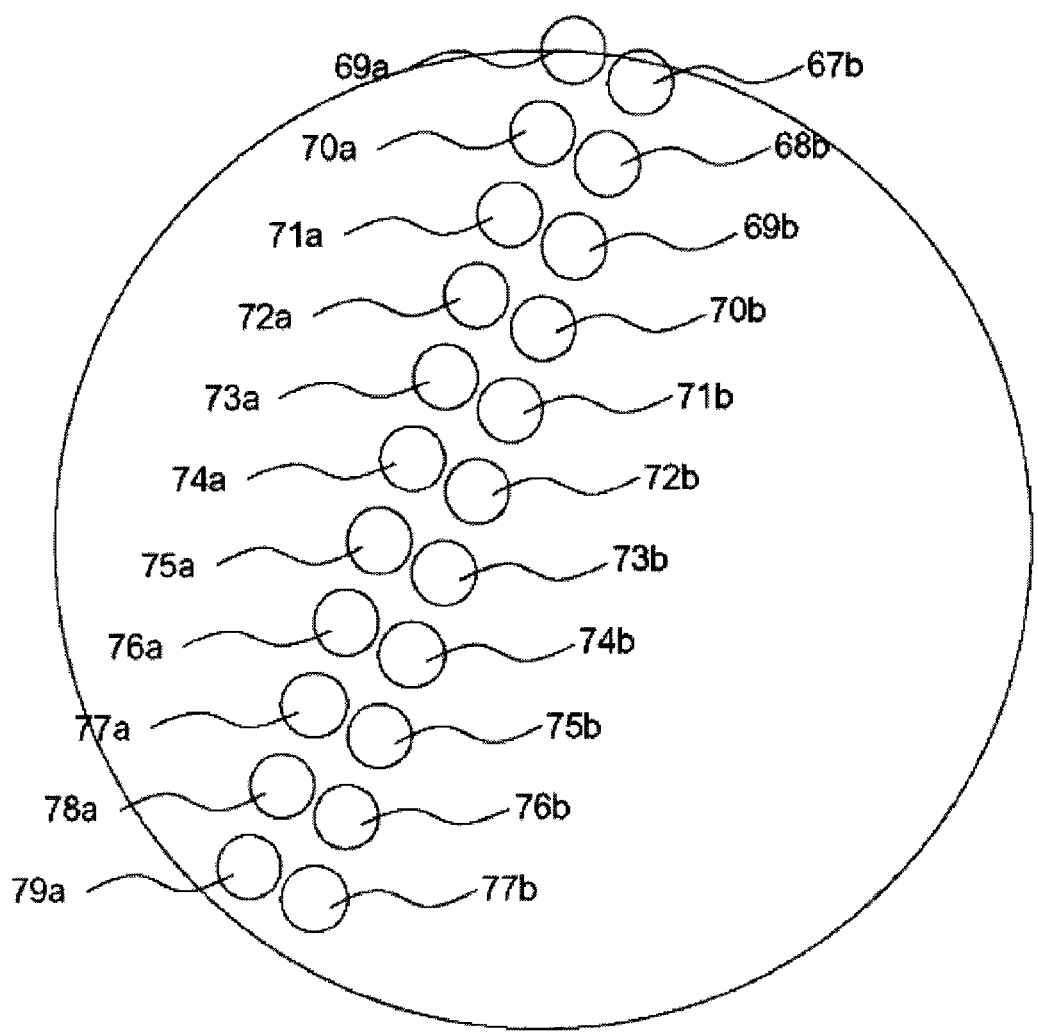
FIG. 7 is a diagram showing another example of diffracted lights on the pupil plane.

However, if the orientation of the wafer 5 (the rotation direction of the wafer 5 surface with respect to the optical axis) is the same as that of the wafer 5 shown in FIGS. 1 and 2, the diffracted lights via the first aperture 62a and via the second aperture 62b are superposed and thereby difficult to distinguish one from the other. Therefore, it is preferable that the stage 6 rotate the wafer 5 by approximately 10 to 20 degrees with the center of the wafer 5 as the rotation center. In this case, the illumination light becomes misaligned with respect to the pattern repetition direction on the wafer 5, as shown in FIG. 7. Because the diffracted lights via the first aperture 62a and the second aperture 62b move rotationally so as to be apart from each other on the pupil plane according to the rotation of the wafer 5, it is possible to separate and detect the diffracted lights via the first aperture 62a and via the second aperture 62b. Further, in FIG. 7, two groups of the diffracted lights are arranged so that one group is shifted in parallel with respect to the other group, the one group including the diffracted lights via the first aperture 62a, namely, the zeroth-order diffracted light 70a, the first-order diffracted light 71a to the ninth-order diffracted light 79a and the negative first-order diffracted light 69a, and the other group including the diffracted lights via the second aperture 62b, namely, the zeroth-order diffracted light 70b, the first-order diffracted light 71b to the seventh-order diffracted light 77b and the negative first-order diffracted light 67b to the negative third-order diffracted light 69b.

Further, in FIG. 7, the zeroth-order diffracted light 70a, the first-order diffracted light 71a to the ninth-order diffracted light 79a and the like via the first aperture 62a correspond to the aforementioned diffracted light H due to high incidence angle. Likewise, the zeroth-order diffracted light 70b, the first-order diffracted light 71b to the seventh-order diffracted light 77b and the like via the second aperture 62b correspond to the aforementioned diffracted light L due to low incidence angle.

However, with respect to the optimum incidence angle for obtaining the diffracted light L due to low incidence angle, it is preferable to obtain diffracted lights which relatively include more baselayer information but almost do not include information regarding the changes of the surface condition of the uppermost layer 500 (the variations in the pattern profile and CD value of the contact holes 510 due to focal error and error in exposure amount in the exposure process). The incidence angle condition satisfying the above requirement is not necessarily the same at all times, but is determined by many physical quantities difficult to calculate such as the film type, the film thickness, the pattern types of the uppermost layer and base layers (line and space or contact holes), the repetition pitch and the like for configuring the wafer 5. For this reason, it is required to determine the optimum incidence angle for obtaining the diffracted light L due to low incidence angle according to the process structure developed for each generation of semiconductor wafers (the DRAM generation of 72 nm, 68 nm, 54 nm and the like; the flash memory generation of 50 nm, 40 nm, 30 nm and the like). Further, as for the same type and the same generation, it is also required to determine the optimum incidence angle for obtaining the diffracted light L due to low incidence angle according to the processes for gate wires, bit lines, bit contacts, capacitor contacts and the like. Here, as an evolutionary type of the deformation aperture stop 61 having the two apertures 62a and 62b, FIGS. 8A to 9B show an effective variable deformation aperture stop 63 for variable low incidence angles.

Figure 8B:
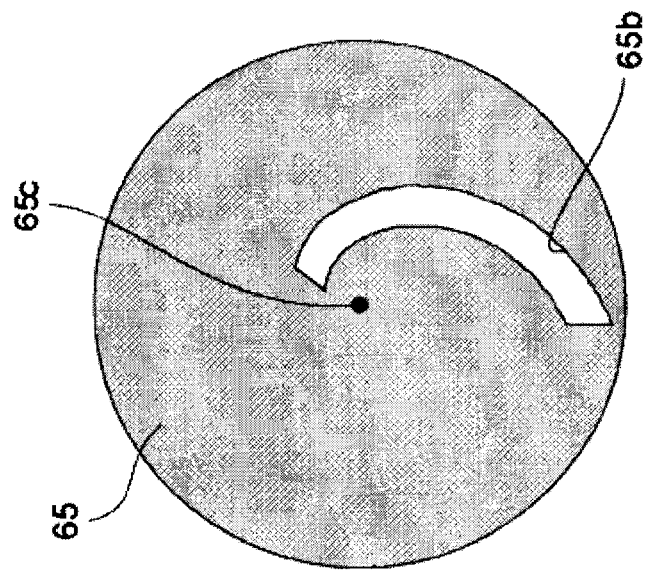
FIGS. 8A and 8B are exploded diagrams of a variable deformation aperture stop.
Figure 8A:
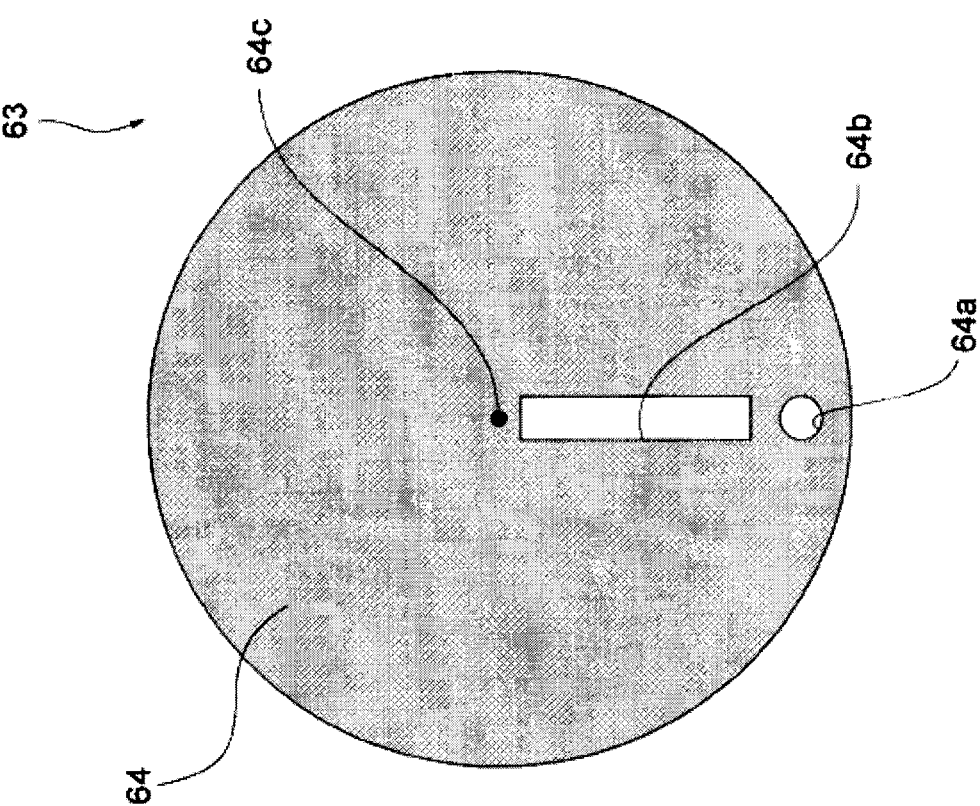

The variable deformation aperture stop 63 is configured to have a fixed deformation aperture stop 64 shown in FIG. 8A and a rotary deformation aperture stop 65 shown in FIG. 8B. In FIGS. 8A and 8B these components are shown separately, in reality, the fixed deformation aperture stop 64 and the rotary deformation aperture stop 65 are superimposed so that the centers of both circles are concentric. The variable deformation aperture stop 63 has the same function as the deformation aperture stop 61 having the two apertures 62a and 62b. As shown in FIG. 8A, a first aperture 64a for a high incidence angle, and a first elongated hole 64b which extends in a radial direction at an inner side of the first aperture 64a (at a side of the optical axis) are formed in the fixed deformation aperture stop 64 which is formed in a disk shape. Further, the center 64c of the fixed deformation aperture stop 64 is in accord with the optical axis.

Figure 9A:
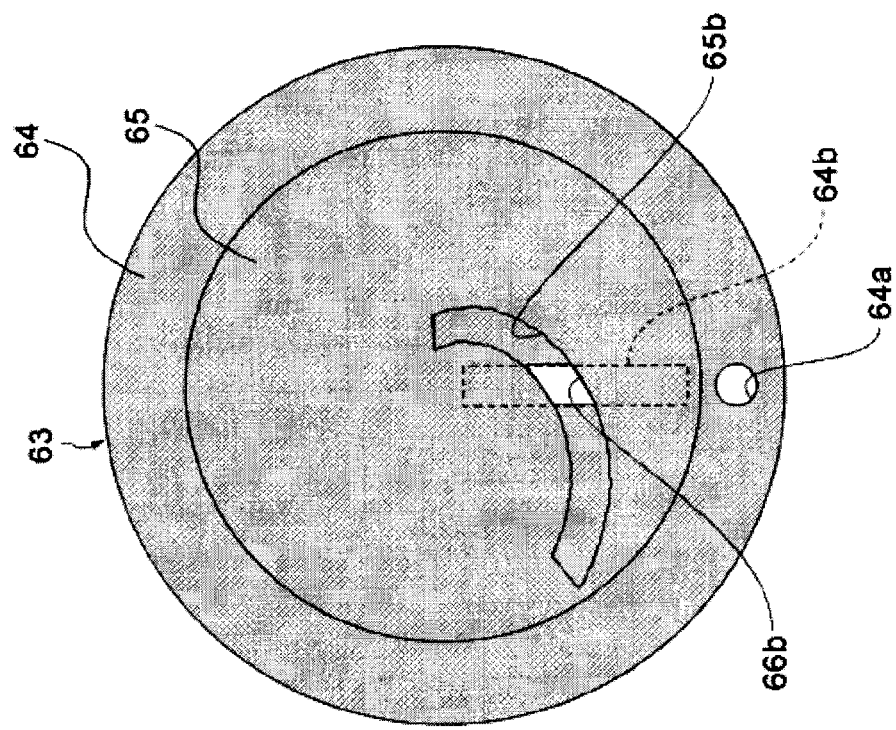
FIGS. 9A and 9B are diagrams showing the variable deformation aperture stop.
Figure 9B:
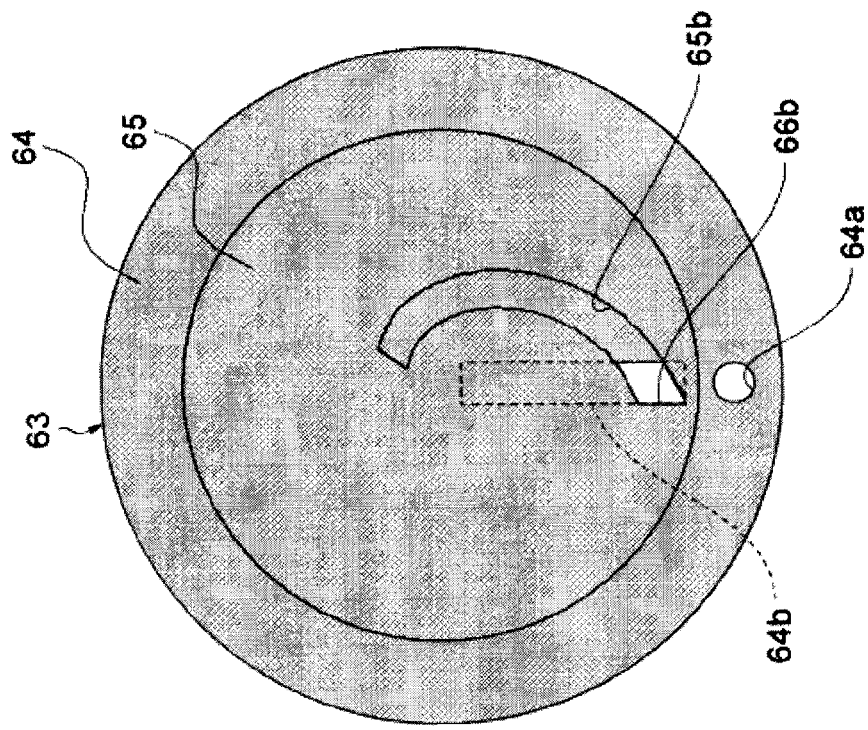

As shown in FIG. 8B, the rotary deformation aperture stop 65 formed in a disk shape is configured to be rotatable with the center 65c of the rotary deformation aperture stop 65 (in accord with the optical axis) as the rotation center. In the rotary deformation aperture stop 65, a second elongated hole 65b is formed in the shape of a mirror-reversed C. The second elongated hole 65b is set so that the distance from the center 65c varies with the rotation angle of the rotary deformation aperture stop 65. In FIG. 9A, the fixed deformation aperture stop 64 and the rotary deformation aperture stop 65 are superposed so that the respective centers 64c and 65c are at the same point. As is understood from the FIG. 9A, a second aperture 66b for low incidence angles is formed by overlapping the first elongated hole 64b and the second elongated hole 65b, and changes in the distance from the optical axis according to the rotation of the rotary deformation aperture stop 65, as shown from FIG. 9A to FIG. 9B for example. Therefore, when the diffracted light L due to low incidence angle is obtained, it is possible to set the optimum condition for low incidence angles by rotating the rotary deformation aperture stop 65 to change the incidence angle.

Next, explanations will be made with respect to some principles and algorithm utilizing a reference wafer in the surface inspection method in accordance with the embodiment. Here, in order to explain these principles and algorithm, some measuring and processing results will be presented with respect to a reference wafer 100 as shown in FIG. 11.

Figure 11:
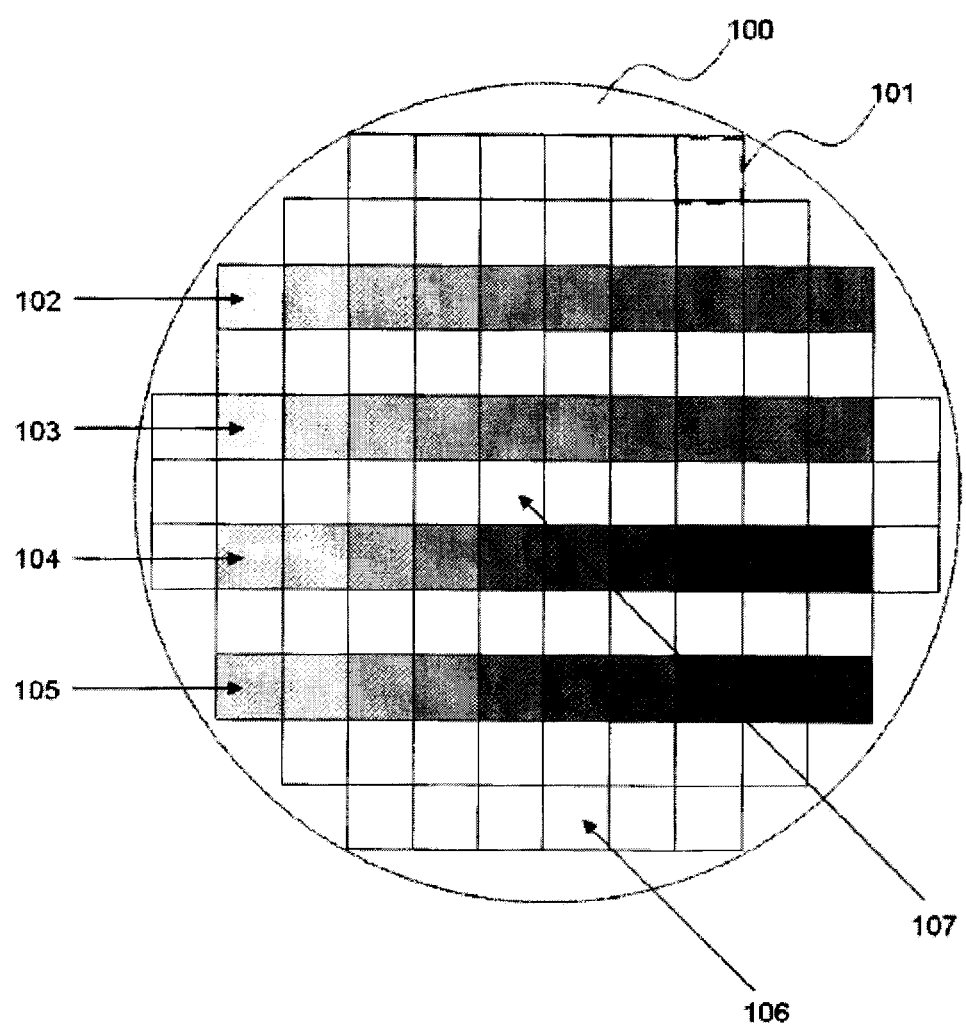
FIG. 11 is a schematic diagram of a reference wafer.

The reference wafer 100 has totally 104 areas of exposure shots 101 one of which is encircled with dashed lines, wherein the third shot row 102 and the fifth shot row 103 located respectively on the third row and the fifth row from above in FIG. 11 are shots exposed with sequentially increased exposure light amount (to be referred to as shots of high exposure light amount; totally 20 shots). Further, the seventh shot row 104 and the ninth shot row 105 located respectively on the seventh row and the ninth row from above in FIG. 11 are shots exposed with sequentially decreased exposure light amount (to be referred to as shots of low exposure light amount; totally 20 shots). Then, shots other than the shots of high exposure light amount and the shots of low exposure light amount (the shot 106, for example) are all those exposed with a standard exposure light amount (to be referred to as shots of standard exposure light amount; totally 64 shots). As a result, the CD value (the diameter of contact holes or the line width of line and space) changes or varies in the third shot row 102, the fifth shot row 103, the seventh shot row 104, and the ninth shot row 105.

Alternatively, the pattern profile may be changed by a manner as described below. That is, the reference wafer 100 is defocused in exposure so that the third shot row 102 and the fifth shot row 103 become shots exposed with sequentially plus-inclined defocus amount (plus defocus shots), that the seventh shot row 104 and the ninth shot row 105 become shots exposed with sequentially minus-inclined defocus amount (minus defocus shots), and that the other shots (the shot 106, for example) become those exposed with the best focus condition (best focus shots). The reference wafer obtained in this manner is measured by the aforementioned CD-SEM. The measured result can be qualified, for example, as the CD value according to the variation in exposure amount. In the following explanations, a case of variation in exposure light amount will be shown. However, it is possible to apply the embodiment to defocus defect inspection and measurement utilizing the defocused reference wafer.

The reference wafer 100 is measured in the following manner. First, by moving the stage 6, the pupil images of all 104 shots are measured by 12 points (horizontal 4 points×vertical 3 points) in each shot. As a result, 12×104=1248 pupil images are obtained. In the surface inspection device 1 shown in FIGS. 1 and 2, 1248 pupil images such as those shown in FIG. 4A are obtained by the high NA objective lens 8a, while 1248 pupil images such as those shown in FIG. 4B are obtained by the low NA objective lens 8b. Further, in the surface inspection device 50 shown in FIG. 5, 1248 pupil images such as those shown in FIG. 7 are obtained.

Since the pupil images of the diffracted lights (41a and the like), in which a suffix 'a' is assigned to the number thereof as shown in the pupil images of FIG. 4A or FIG. 7, are obtained by the diffracted light H due to high incidence angle, the optimum-order diffracted lights are selectively extracted from the obtained pupil images. In the same manner, since the pupil images of the diffracted lights (41b and the like), in which a suffix 'b' is assigned to the number thereof as shown in the pupil images of FIG. 4B or FIG. 7, are obtained by the diffracted light L due to low incidence angle, the optimum-order diffracted lights are selectively extracted from the obtained pupil images. Further, the method for determining the optimum order will be described hereinafter.

Figure 12:
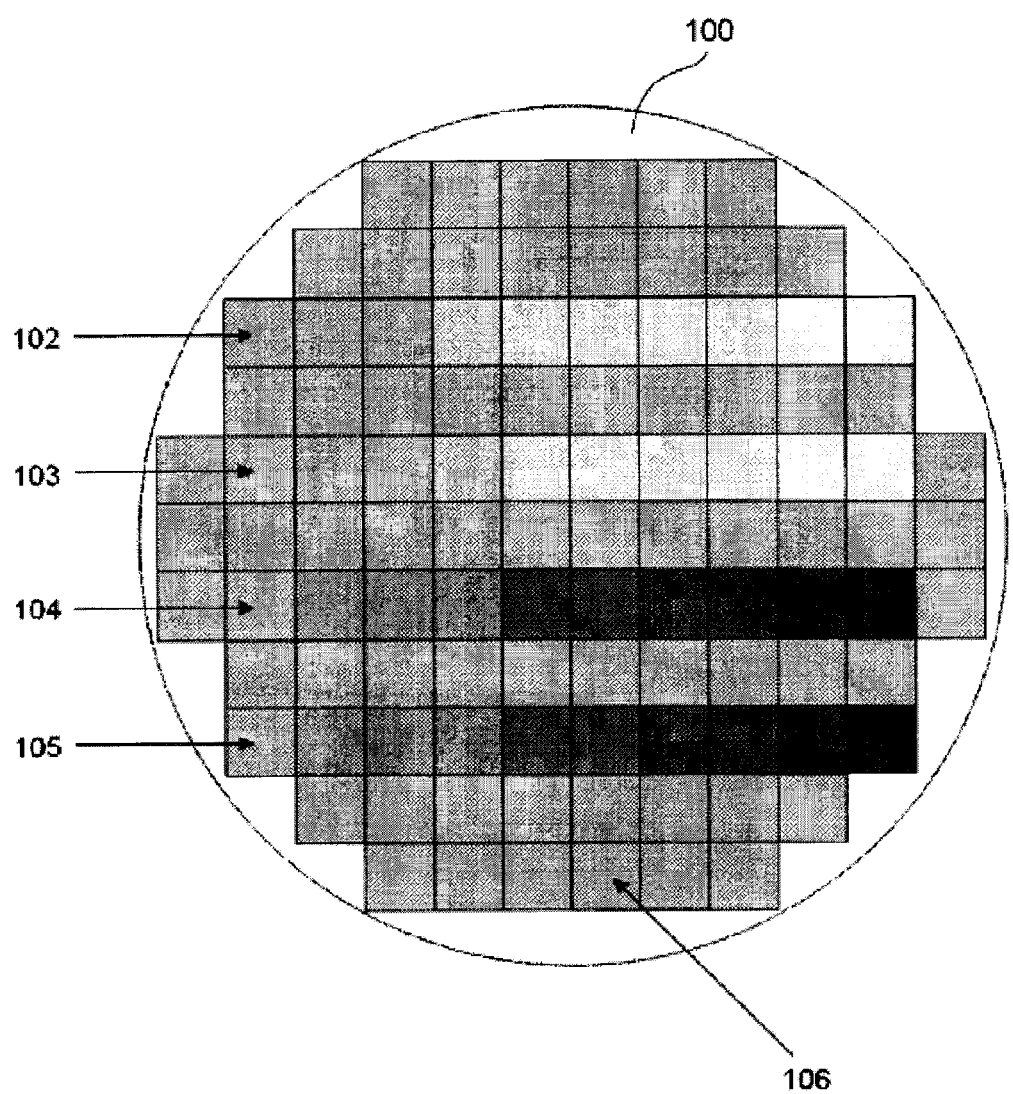
FIG. 12 is a schematic diagram showing a brightness distribution of the diffracted lights supposed to arise on the reference wafer.
Figure 13:
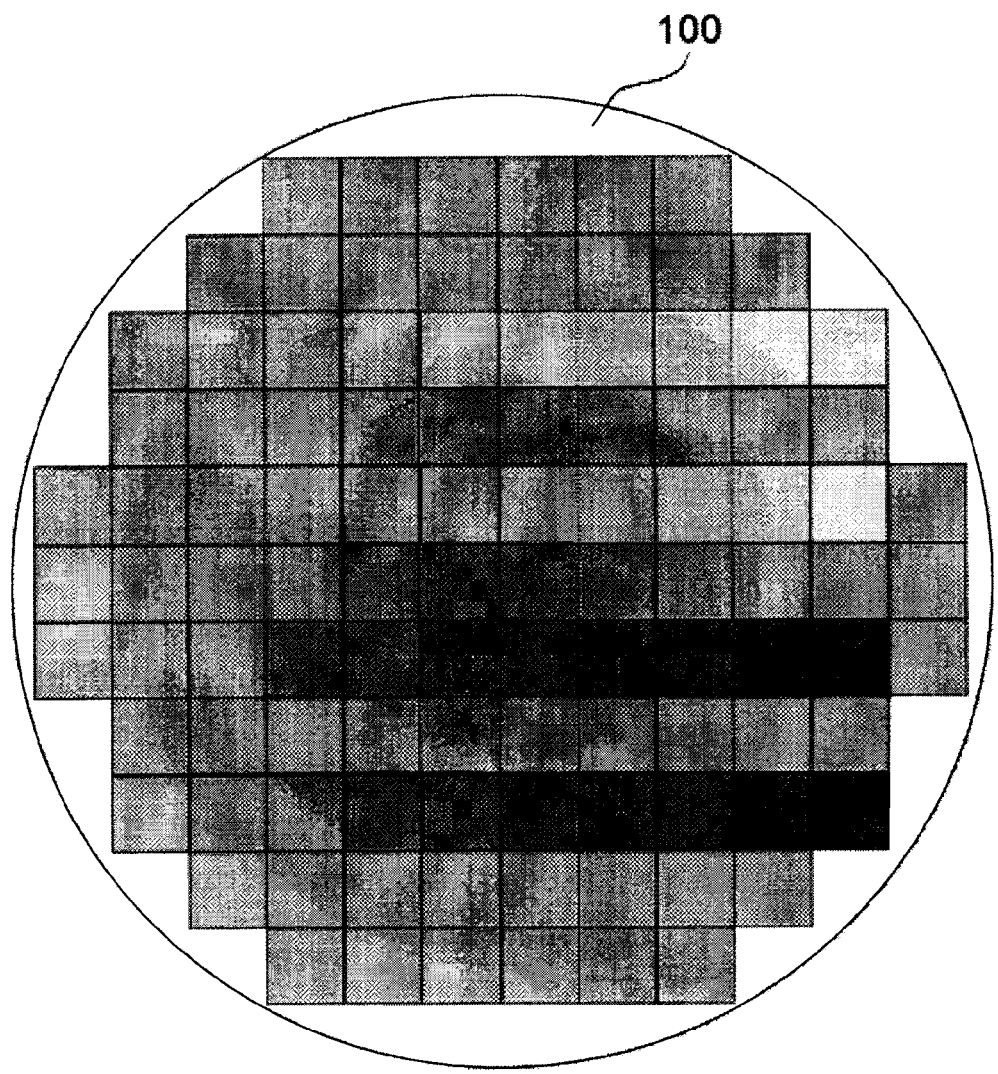
FIG. 13 is a schematic diagram showing an observed brightness distribution of the diffracted lights on the reference wafer.
Figure 34A:
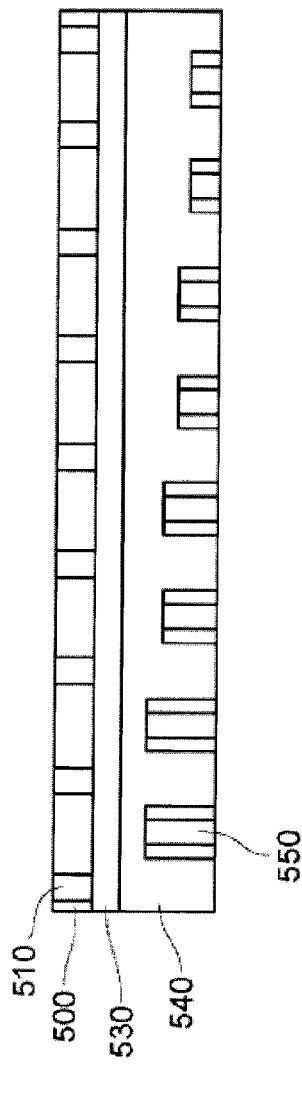
FIGS. 34A to 34C are diagrams showing an example of each layer formed in the wafer surface.
Figure 34B:
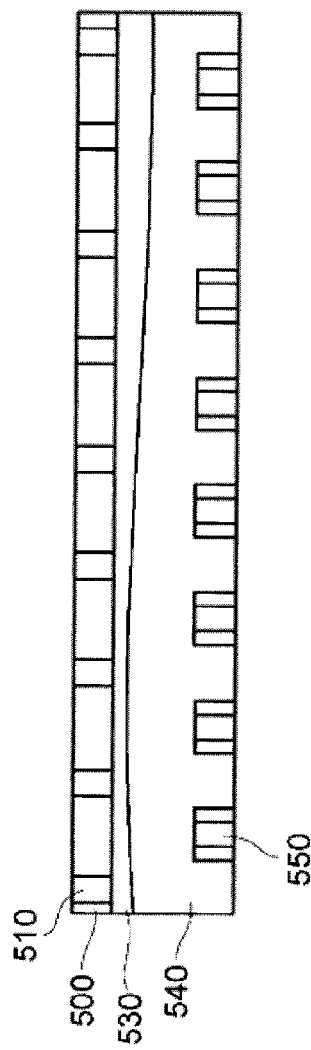
Figure 34C:
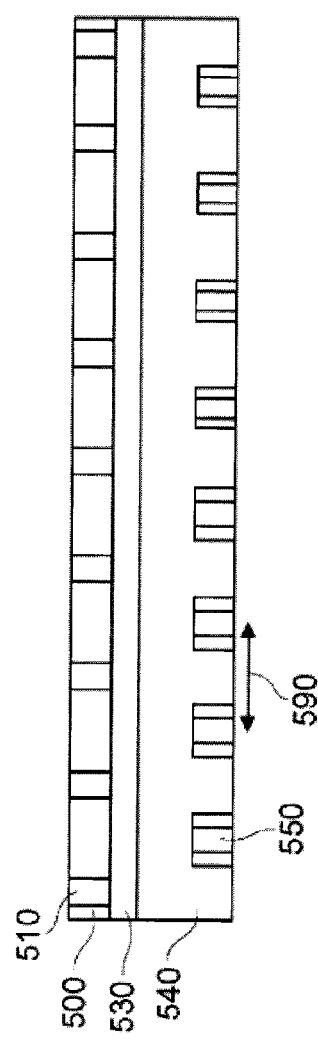

FIGS. 12 and 13 show the brightness of the diffracted light H due to high incidence angle (the first-order diffracted light H1, for example) which is selectively extracted from the 1248 pupil images and is spread on 1248-point wafer coordinates as a map. In particular, since the 1248-point wafer coordinates can be obtained from the 12-point coordinates in each shot and the position coordinates of the shot, it is possible to spread the brightness of the 1248-point diffracted light H due to high incidence angle on the wafer coordinate system. For example, FIGS. 12 and 13 can be obtained by making a brightness contour map on the wafer coordinate system. Because the CD value changes in the shot rows 102, 103, 104 and 105 with changed exposure light amount, the diffracted light H due to high incidence angle becomes brighter or darker than the standard shot 106 according to the CD value. However, while FIG. 12 shows the case without the baselayer-influence, the multilayer films as shown in FIGS. 33 to 34C are under the baselayer-influence. Therefore, the diffracted light H due to high incidence angle takes on an uneven brightness within the wafer surface as shown in FIG. 13. Further, in FIG. 13, with respect to the reference wafer 100, the vicinity of the center is dark and, furthermore, the upper right portion is darker than the lower left portion. In this manner, as has already been described, difference occurs in the average brightness on the wafer surface and in the uneven brightness within the wafer surface according to each wafer, or according to each lot.

Figure 14:
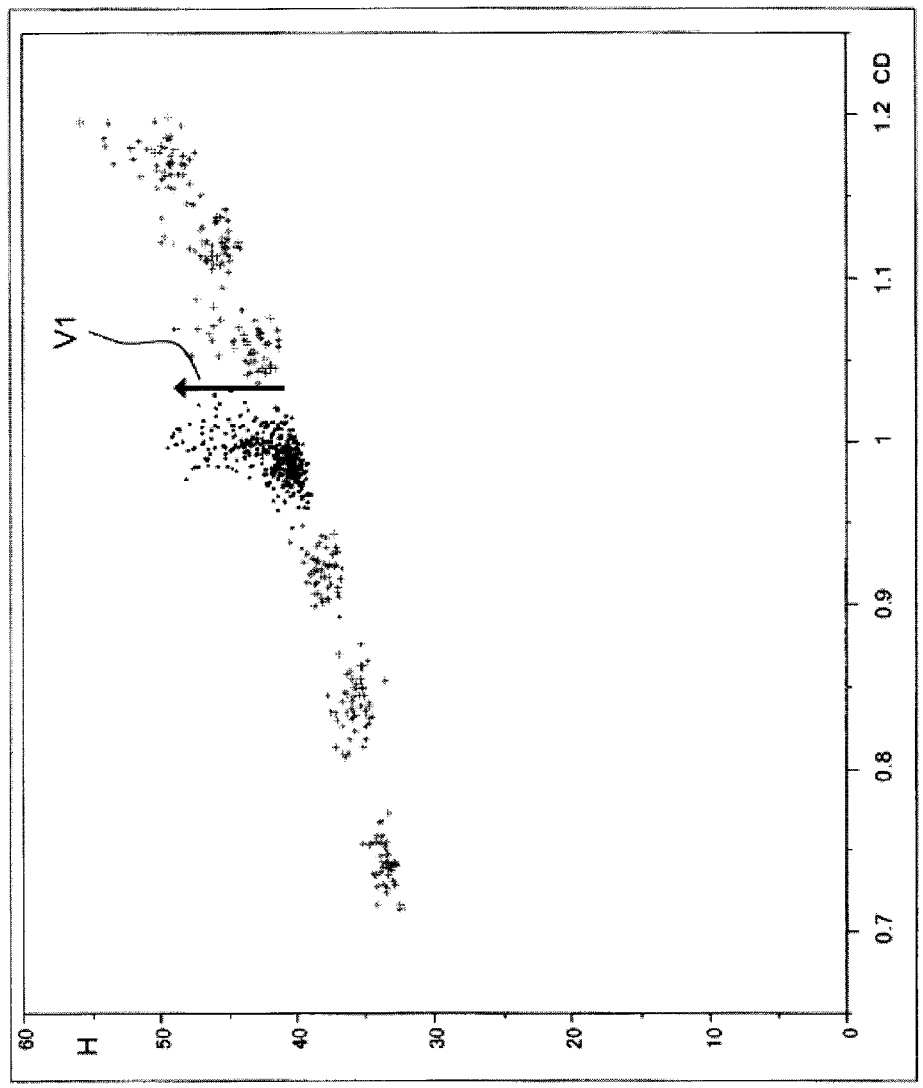
FIG. 14 is a diagram showing a relation between a CD value and diffracted lights due to the high incidence angle.

In the plot shown in FIG. 14, the horizontal axis indicates the CD value measured by a CD-SEM, and the vertical axis indicates the brightness value of the diffracted light H due to high incidence angle, for all measuring points (1248 points). The black dots show the results of measuring the shots of standard exposure light amount (64 shots×12 points=768 points), while the gray crosses show the results of measuring the shots of high exposure light amount and the shots of low exposure light amount (40 shots×12 points=480 points in total). The CD value on the horizontal axis in FIG. 14 is normalized by the average of the CD value obtained by shots of standard exposure light amount. The average of the CD value is normalized as 1. As is understood from FIG. 14, the larger the CD value, the larger the diffracted light H due to high incidence angle. This is due to the fact in which the diffracted lights depend on the variation in CD value, because the diffracted light H due to high incidence angle includes comparatively more of the signals from the uppermost layer 500. However, because the baselayer-influence varies with the position within the wafer surface, the diffracted light H due to high incidence angle fluctuates in brightness value even in the vicinity of the same CD value=1 (in FIG. 14, the fluctuation in the value of the diffracted light H due to high incidence angle at the CD value=1 is shown as a vector V1).

Especially, the fluctuation of the diffracted light H due to high incidence angle in the shots of standard exposure light amount shown with the black dots is larger than that of the diffracted light L due to low incidence angle in the shots of high and low exposure light amounts shown with the gray crosses. Because the shots of standard exposure light amount occupy more area of the wafer on the outer circumferential side, the baselayer-influence becomes more obvious in the outer area to the circumference of the wafer, and the signal from the base layers is superimposed on the diffracted light H due to high incidence angle. The fluctuation of the diffracted light H due to high incidence angle in the shots of standard exposure light amount (black dots) is approximately 10 (10 is obtained by reading the scale on the vertical axis), and this value corresponds to approximately 0.4 of the change in normalized CD value on the horizontal axis. In other words, in spite of the CD value=1, since the diffracted light H due to high incidence angle is affected by the base layers, the CD value may be regarded as if changing approximately 40%. In this situation, it is not possible to detect the change in CD value correctly.

Figure 15:
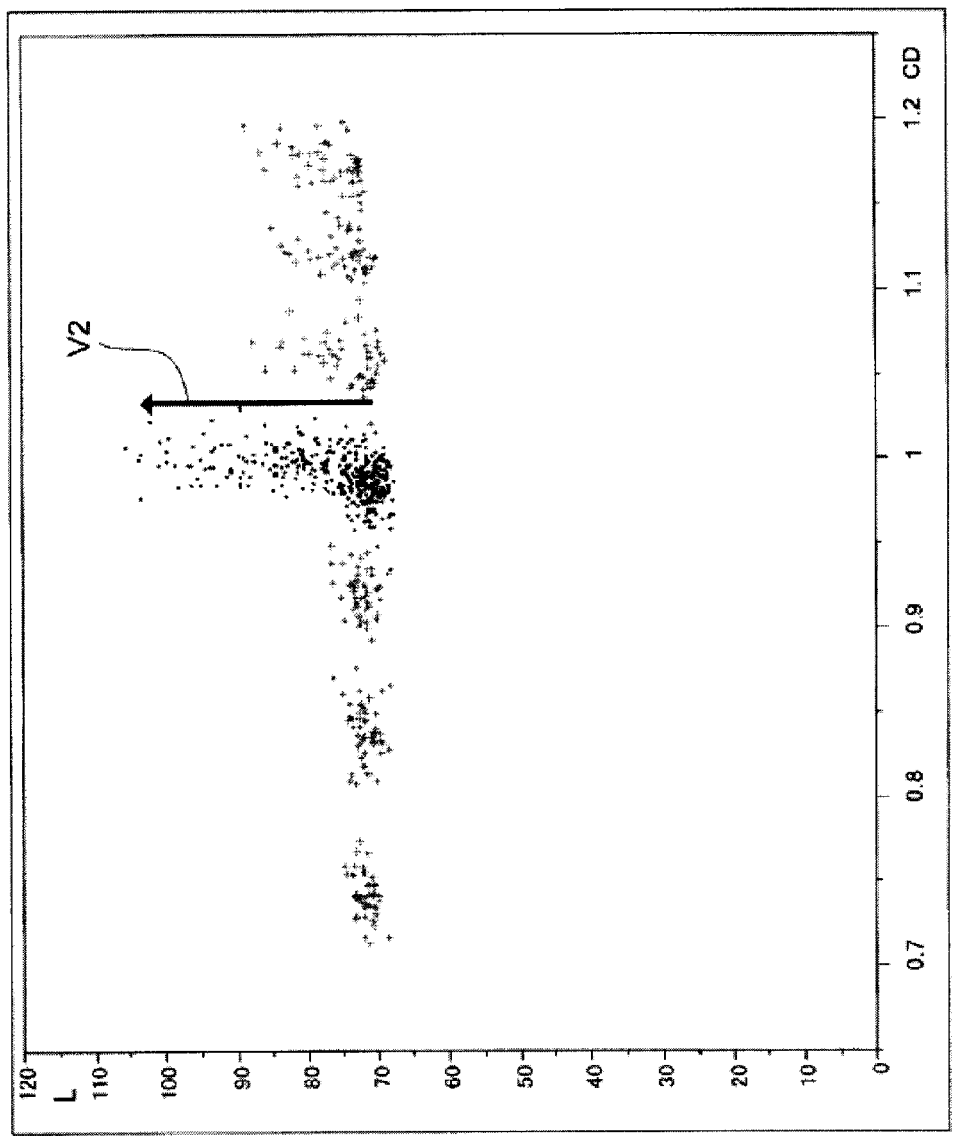
FIG. 15 is a diagram showing a relation between the CD value and diffracted lights due to the low incidence angle.

In the plot shown FIG. 15, the horizontal axis indicates the CD value measured by a CD-SEM, and the vertical axis indicates the brightness value of the diffracted light L due to low incidence angle, for all measuring points (1248 points). In the same manner as FIG. 14, the black dots show the results of measuring the shots of standard exposure light amount (64 shots×12 points=768 points), while the gray crosses show the results of measuring the shots of high exposure light amount and the shots of low exposure light amount (40 shots×12 points=480 points in total). Further, still in the same manner as FIG. 14, the CD value on the horizontal axis in FIG. 15 is normalized with the average of the CD value, which is normalized as 1, obtained by shots of standard exposure light amount. As is understood from FIG. 15, even if the CD value changes, the diffracted light L due to low incidence angle does not change in brightness value. Because the diffracted light L due to low incidence angle includes only a few of the signals from the uppermost layer 500, and thereby does not depend on the change in CD value. That is, most of the diffracted light L due to low incidence angle is sensitive to the underlayer information. Further, because the baselayer-influence per se is reflected by the position within the wafer surface, the diffracted light L due to low incidence angle fluctuates in value even at the same CD value=1 (In FIG. 15, the fluctuation in the value of the diffracted light L due to low incidence angle at the CD value=1 is shown as a vector V2).

Hereinbelow, references will be made to three of the four principles discovered by the present inventor.

The first principle: The diffracted light H due to high incidence angle is sensitive to the variation in CD value, and includes the baselayer-influence.

The second principle: The diffracted light L due to low incidence angle is insensitive to the variation in CD value, but includes the baselayer-influence.

The third principle: It is possible to eliminate or correct the baselayer-influence under a condition in which the influential inclination from the base layers within the wafer surface for the diffracted light H due to high incidence angle is similar to (has a similarity relationship with) the influential inclination from the base layers within the wafer surface for the diffracted light L due to low incidence angle.

Since the first principle and the second principle have already been described, the third principle will be explained hereinbelow. Further, the measuring results shown in FIGS. 14 and 15 are obtained under the optimum condition (wavelength, incidence angle, and order of diffracted lights) in which the first to third principles are satisfied. Further, the method for determining the optimum condition will be described hereinafter in detail.

Figure 16:
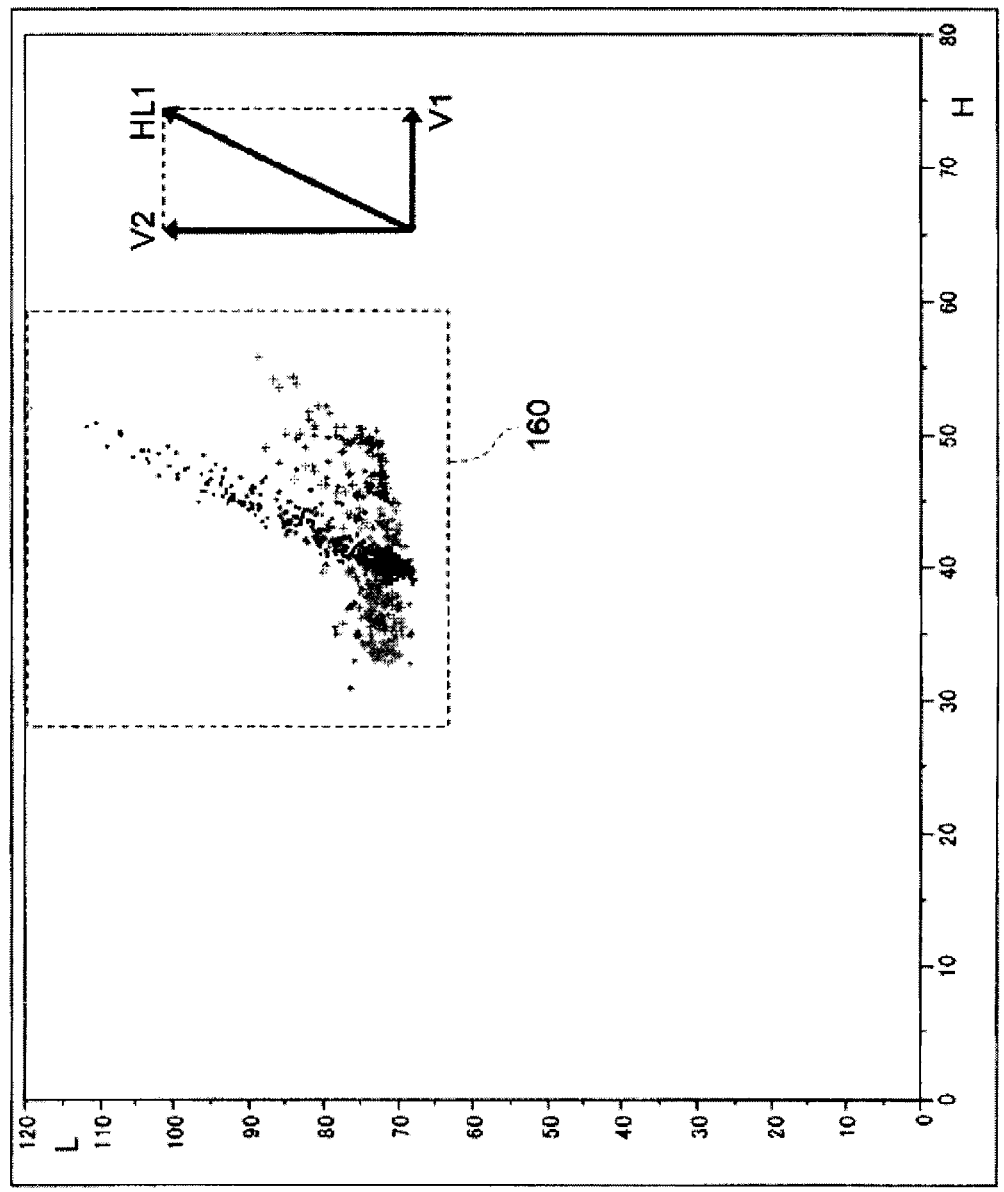
FIG. 16 is a diagram showing a relation between the diffracted lights due to the high incidence angle and the diffracted lights due to the low incidence angle.

In FIG. 16, the brightness values of the diffracted light H due to high incidence angle and the diffracted light L due to low incidence angle are plotted on the horizontal axis and the vertical axis, respectively, with respect to each of the measuring points (1248 points). In FIG. 16, the measuring points for the shots of standard exposure light amount which are indicated by the black dots distribute in an obliquely upward direction to the right, due to the baselayer-influence. The obliquely upward direction to the right is the direction of the resultant vector HL1 of composing or adding the vector V1 of the fluctuation of the diffracted light H due to high incidence angle at the CD value=1 and the vector V2 of the fluctuation of the diffracted light L due to low incidence angle at the CD value=1. Especially, since the third principle that "a condition in which the influential inclination from the base layers within the wafer surface for the diffracted light H due to high incidence angle is similar to the influential inclination from the base layers within the wafer surface for the diffracted light L due to low incidence angle" is satisfied, a very strong correlation along the resultant vector HL1 is observed. On the other hand, the shots of high and low exposure light amounts shown in FIG. 16 with the gray crosses distribute in a horizontal row, because the diffracted light H due to high incidence angle become large with respect to the change in CD value, but the diffracted light L due to low incidence angle almost do not change with respect to the change in CD value.

Figure 17:
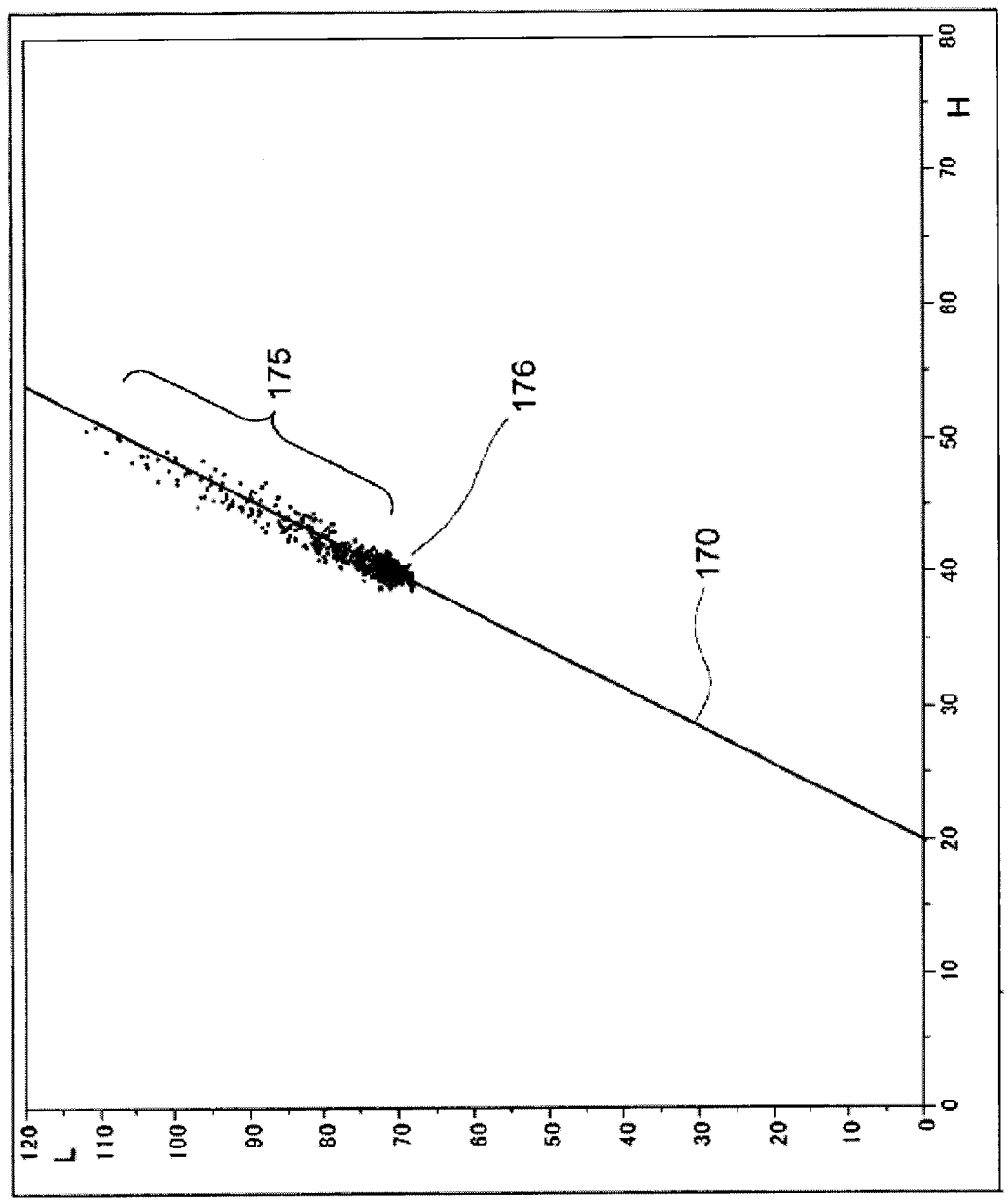
FIG. 17 is a diagram showing a relation between the diffracted lights due to the high incidence angle and the diffracted lights due to the low incidence angle with respect only to the shots of a standard exposure amount.

In FIG. 17, only the points of measuring the shots of standard exposure light amount are plotted on the diffracted light H due to high incidence angle (horizontal axis) and the diffracted light L due to low incidence angle (vertical axis). When the brightness values are denoted respectively by H and L, the linear regression line 170 according to the least-square method is expressed by the following equation (1).

$$L = -70.0 + (3.51 \times H) \tag{1}$$

Since the equation (1) represents the third principle, the inverse function of the equation (1) shows the baselayer component of the diffracted light H due to high incidence angle to be obtained from the diffracted light L due to low incidence angle. That is, it is possible to obtain a value from the measured diffracted light L due to low incidence angle by using the inverse function of the equation (1), the value corresponding to the baselayer component of the diffracted light H due to high incidence angle that is calculated based on the correlation between the diffracted light H due to high incidence angle and the diffracted light L due to low incidence angle. The value is referred to as 'baselayer correction value H*'. Specifically, the diffracted light H due to high incidence angle and the diffracted light L due to low incidence angle are obtained in each measuring point. In this case, with respect to the measured diffracted light L due to low incidence angle, the baselayer correction value H* is expressed by the following equation (2), that is the inverse function of equation (1).

$$H^* = 19.9 + (0.285 \times L) \tag{2}$$

As described above, this baselayer correction value H* corresponds to the baselayer signals of the diffracted light H due to high incidence angle calculated from the measured diffracted light L due to low incidence angle, and is named as the baselayer correction value. Therefore, the value of subtracting the baselayer correction value H* from the measured diffracted light H due to high incidence angle is that of having eliminated the baselayer signals, and expressed by the following equation (3).

$$H - H^* \tag{3}$$

However, the equation (3) has only eliminated the uneven baselayer-influence within the wafer surface, but not yet corrected the uneven fluctuation for each wafer (the baselayer-influence causes the diffracted light H due to high incidence angle to become larger on average throughout the wafer). The latter correction will be described hereinafter.

Figure 18:
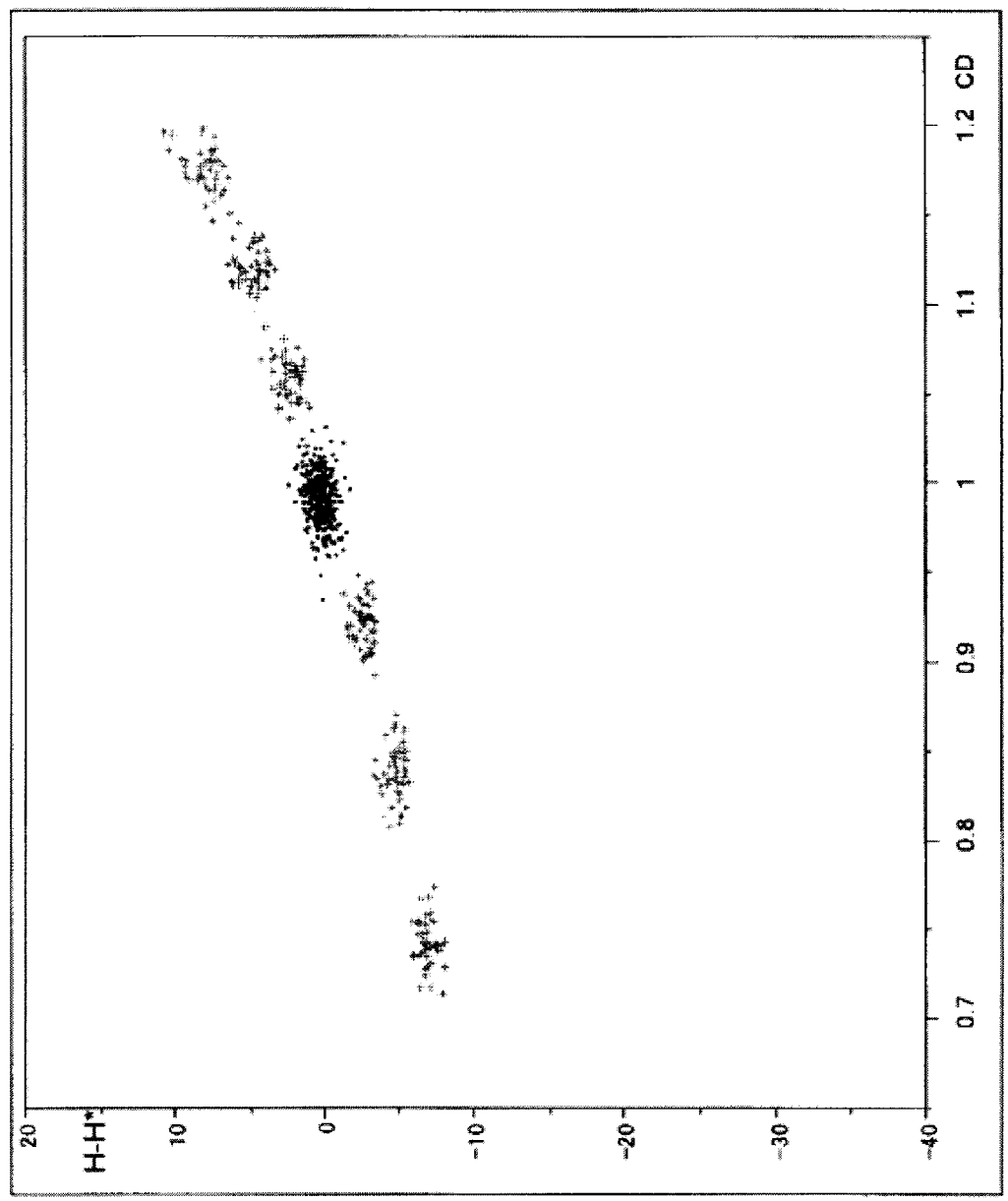
FIG. 18 is a diagram showing a relation between the CD value and a base layer correction signal.

Since the baselayer signals of the reference wafer 100 per se is eliminated in the equation (3). Therefore, as shown in FIG. 18, when the result H−H* calculated by the equation (3) is indicated in the vertical axis and the CD value is indicated in horizontal axis, then the result in which the baselayer-influence is eliminated is obtainable. That is, the measuring points of the shots of standard exposure light amount shown in FIG. 18 with the black dots show the mere fluctuation in measurement, because a stretching upward in the plot (the fluctuation V1 of the diffracted light H due to high incidence angle at the CD value=1) is removed, as a result of having eliminated the baselayer-influence. Likewise, as shown in FIG. 18, a stretching upward is also removed in the plot of the measuring points regarding the shots of high and low exposure light amounts with the gray crosses. Consequently, from the results of the shots of standard exposure light amount and the shots of high and low exposure light amounts, there is a relation of a kind of quadratic curve between the value (H−H*) given by the equation (3) and the CD value. Therefore, the inverse relational expression, that is, the following equation (4), becomes one of the procedures to calculate the CD value.

$$CD=0.987+\{0.0355\times(H-H^*)\}-[0.00101\times\{(H-H^*)-0.0831\}^2] \quad (4)$$

Next, explanations will be made with respect to the principles and algorithm utilizing an actual wafer. With respect to the actual wafer 5, in the same manner as in the case of the reference wafer 100, by moving the stage 6, the pupil images of all 104 shots are measured by 12 points within each shot. When the diffracted light H due to high incidence angle and the diffracted light L due to low incidence angle are obtained from the 1248 pupil images, the diffracted light H due to high incidence angle fluctuates within the surface of the wafer 5 with respect to each wafer and each lot. Hereinbelow, explanations will be made with respect to a means for the underlayer correction and CD value calculation.

Figure 19:
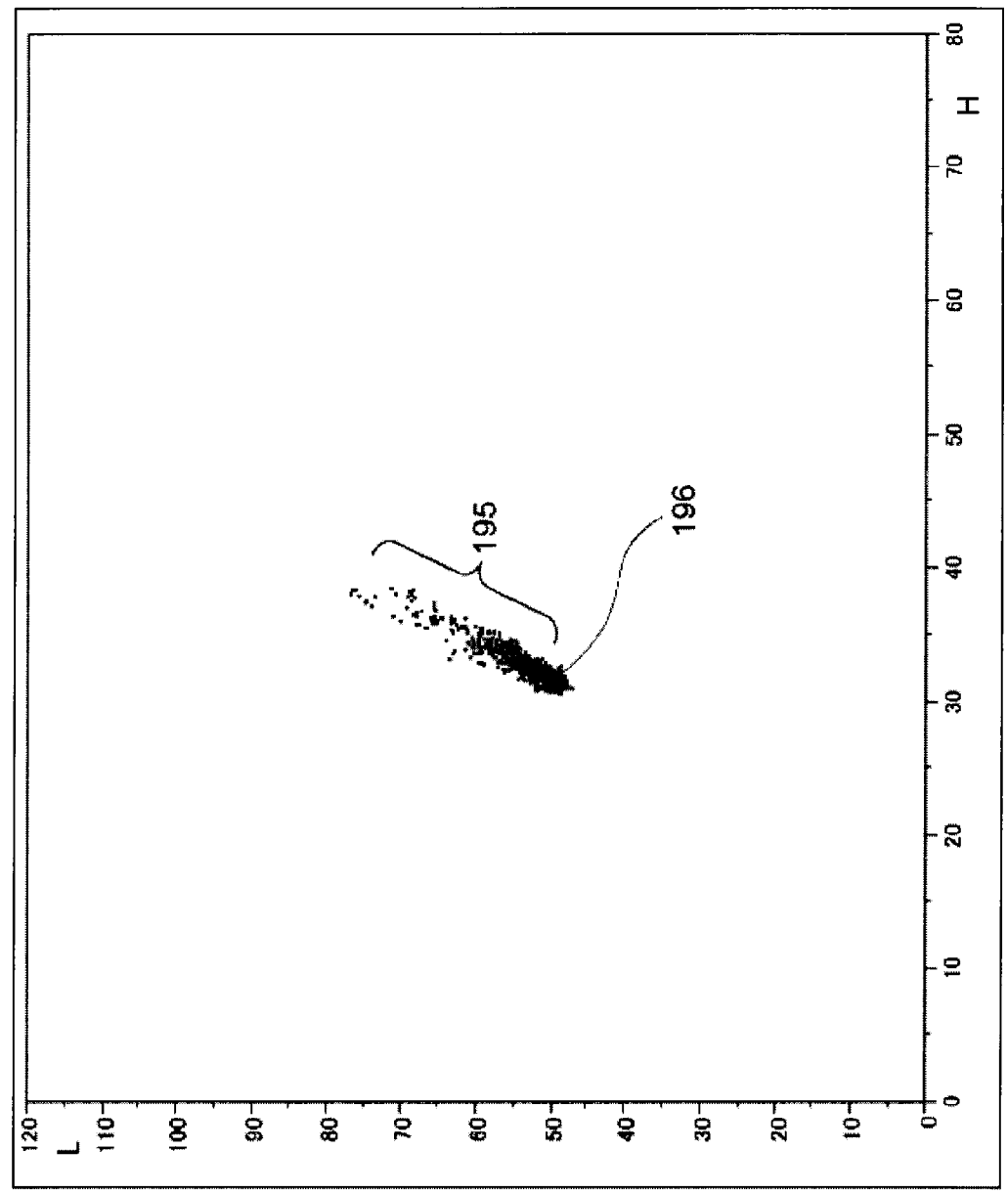
FIG. 19 is a diagram showing a relation between the diffracted lights due to the high incidence angle and the diffracted lights due to the low incidence angle with respect to an actual wafer.
Figure 20:
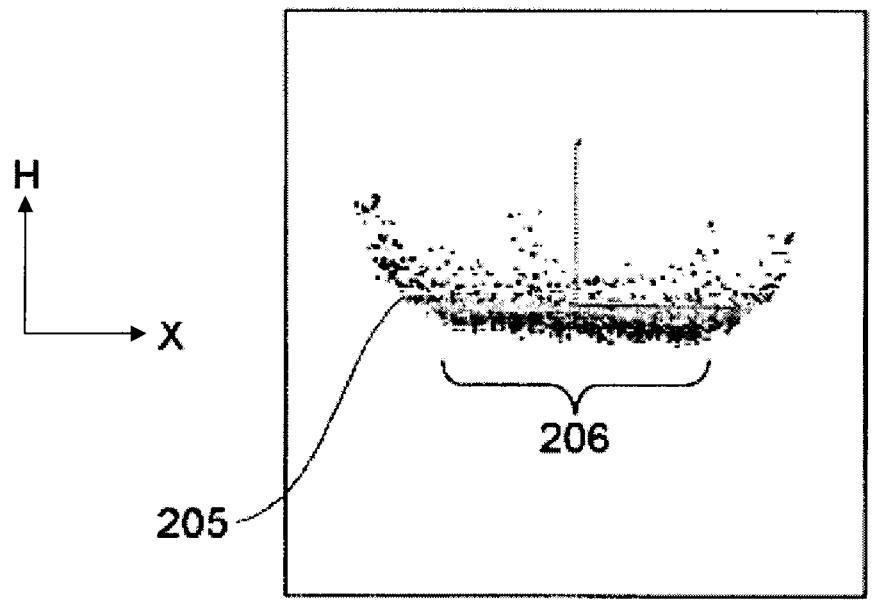
FIG. 20 is a diagram three-dimensionally showing a relation between X coordinate on a wafer surface and the diffracted lights due to the high incidence angle.
Figure 21:
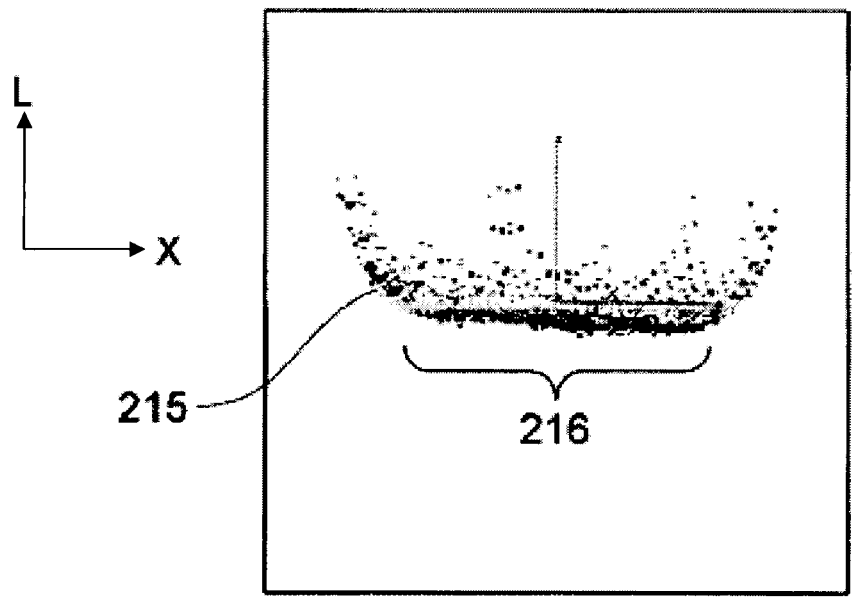
FIG. 21 is a diagram three-dimensionally showing a relation between the X coordinate on the wafer surface and the diffracted lights due to the low incidence angle.

In FIG. 19, the diffracted light H due to high incidence angle (horizontal axis) and the diffracted light L due to low incidence angle (vertical axis) are plotted for 1248 points within a wafer surface of a certain lot. Because the respective baselayer-influences has the same inclination, the diffracted light H due to high incidence angle and the diffracted light L due to low incidence angle are in a linear relation. FIGS. 20 and 21 show the details.

FIG. 20 shows the relation between the X coordinates of the 1248 points on the wafer surface (one axis of a two-dimensional shot array is defined as the X-axis and the other axis is defined as the Y-axis), and the diffracted light H due to high incidence angle. Likewise, FIG. 21 shows the relation between the X coordinates of the 1248 points on the wafer surface and the diffracted light L due to low incidence angle. As is understood from FIGS. 20 and 21, both the diffracted light H due to high incidence angle and the diffracted light L due to low incidence angle have a brightness distribution of the diffracted light turning up at the outer circumferential side of the wafer in a frying-pan-like fashion. Further, trends of both plots resemble with each other. Further, in each of the diagrams, the origin is set at the centroid of the diffracted light H due to high incidence angle and the centroid of the diffracted light L due to low incidence angle, respectively.

Comparing FIG. 19 with FIG. 17, in spite of the similar inclinations, the distributions are different. Specifically, in both FIGS. 17 and 19, a stretched tail in a cometary fashion is shown, and the tails (the tail 195 in FIG. 19 and the tail 175 in FIG. 17) correspond to the frying-pan-like turnups seen in FIGS. 20 and 21 (the frying-pan-like turnup 205 in FIG. 20 and the frying-pan-like turnup 215 in FIG. 21 on the outer circumferential side of the wafer). The comet heads (the head 196 in FIG. 19 and the head 176 in FIG. 17) correspond to the frying-pan bottoms seen in FIGS. 20 and 21 (the frying-pan bottom 206 in FIG. 20 and the frying-pan bottom 216 in FIG. 21 on the inner side of the wafer). Further, the present inventor confirms that the frying-pan-like distribution is always shown under the optimum condition (wavelength, incidence angle, order of diffracted lights and the like) determined in the embodiment. Therefore, it is preferable to utilize the value of the central shot among the exposure shots within the wafer surface, as the representative value for the comet heads (the head 196 in FIG. 19 and the head 176 in FIG. 17). This is because the central shot has a higher possibility of being a non-defective shot.

Figure 22:
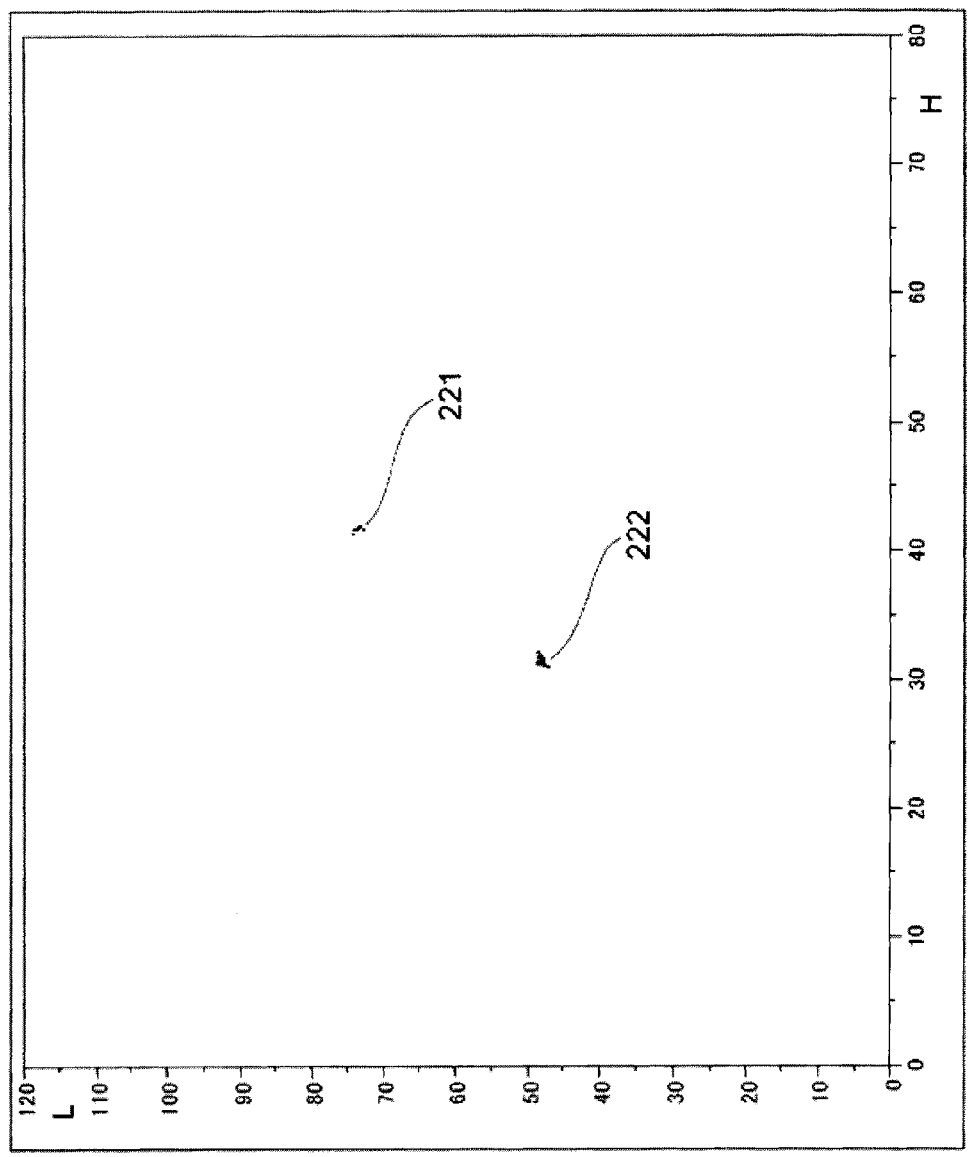
FIG. 22 is a diagram comparing the relation between the diffracted lights due to the high incidence angle and the diffracted lights due to the low incidence angle within a central shot by the reference wafer and the actual wafer.

FIG. 22 shows a relation between the diffracted light H due to high incidence angle and the diffracted light L due to low incidence angle, with respect to the 12 points within the central shot (the central shot 107 in FIG. 11). Further, the group 221 in FIG. 22 is the value for the reference wafer 100, while the group 222 in FIG. 22 is the value for the wafer 5 in a certain lot. As is understood from FIG. 22, the value offsets approximately 10 for the diffracted light H due to high incidence angle, and offsets approximately 30 for the diffracted light L due to low incidence angle. Specifically, although the shapes of the frying-pan-like turnups (the portions of the comet tails) are similar to each other, the value of the frying-pan bottoms (the portions of the frying-pan bottoms) offsets with each other.

Hereinbelow, a reference will be made to the fourth principle discovered by the present inventor.

The fourth principle: the relation between the diffracted light H due to high incidence angle and the diffracted light L due to low incidence angle offsets with respect to each wafer, and it is possible to represent the offset by the central shot of the wafer.

As described hereinbefore, this is because the present inventor confirms that the frying-pan-like distribution (the CD value is considered approximately one for the bottom portion) is always shown under the optimum condition (wavelength, incidence angle, order of diffracted lights and the like) determined in the embodiment. Further, the fourth principle is satisfied in the case in which the optimum condition (wavelength, incidence angle, and order of diffracted lights) is set. The method for determining the optimum condition will be described hereinafter in detail.

Hereinbelow, an offset correction will be explained. First, Hc0 and Lc0 are defined as the average brightness values of the group 221 of the reference wafer 100 for the diffracted light H due to high incidence angle and the diffracted light L due to low incidence angle, respectively. Further, the 'c' included in the notations stands for the central shot. Then, in the H-L coordinate system, (Hc0, Lc0)=(41.27, 72.65). Likewise, Hca and Lca are defined as the average brightness values of the group 222 of the wafer 5 in a certain lot for the diffracted light H due to high incidence angle and the diffracted light L due to low incidence angle, respectively. Then, in the H-L coordinate system, (Hca, Lca)=(31.60, 47.86).

Next, a linear transformation will be carried out based on the offsets of the central shots with respect to the diffracted light H due to high incidence angle and the diffracted light L due to low incidence angle, i.e., (Hc0−Hca) and (Lc0−Lca), for all measuring points (1248 points). In particular, when Ha and La are defined as the measuring values (brightness values) of the diffracted light H due to high incidence angle and the diffracted light L due to low incidence angle, respectively, the following equations (5) and (6) are utilized to carry out the linear transformation for each measuring point.

$$H=Ha+(Hc0-Hca) \quad (5)$$

$$L=La+(Lc0-Lca) \quad (6)$$

Next, the H obtained by the equation (5) is applied to the equation (3). Further, the H* in the equation (3) is obtained by applying the L obtained by the equation (6) to the equation (2). Then, by applying the H–H* obtained by the equation (3) to the equation (4), it is possible to obtain the CD value. Further, after finding the CD value in this manner, if the found CD value changes more than the target CD value over a threshold value, the computation processing section 30 can determine that the corresponding shot is a defective shot. By virtue of this, it is possible to detect detects (or inspect defects) on the surface of the wafer 5.

Based on the calculation as described above, a conclusion may be drawn for the wafer 5 in a certain lot. Further, it is common to all CD value diagrams that normalization is made on the CD value average (CD value=1) with respect to the shots of standard exposure light amount.

Figure 23:
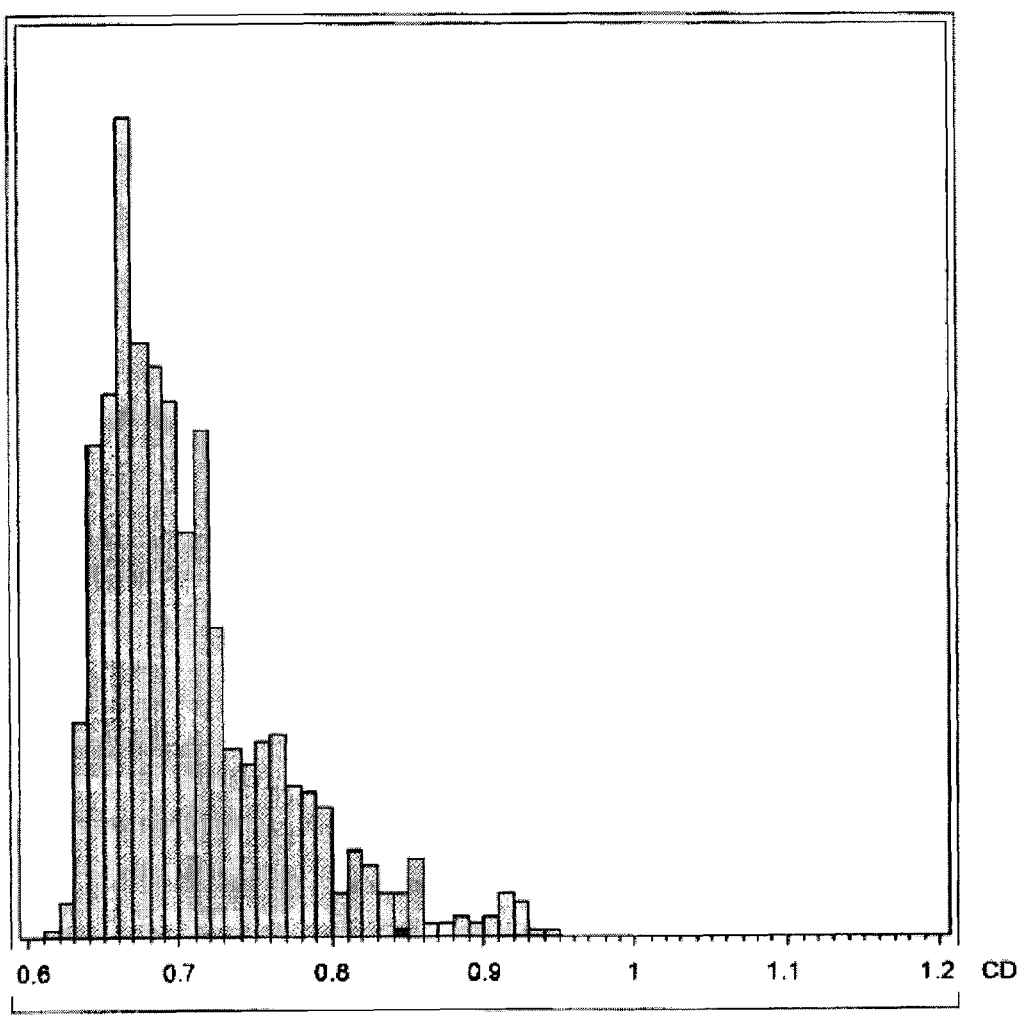
FIG. 23 is a histogram showing the CD value calculated by utilizing the relation of FIG. 14 for the actual wafer.

FIG. 23 shows the CD values calculated by utilizing the relation of FIG. 14 for the wafer 5 in a certain lot. In FIG. 23, correction for the uneven baselayer-influence within the wafer surface (the frying-pan-like turnups) and correction regarding each wafer are insufficient. As a result, the average CD value is approximately 0.63, and the standard deviation is approximately 0.075. Commonly, because the shift should be within ±10% in the standard, if an overall 37% is shifted (1−0.63=0.37), even a normal wafer will be determined as defective, and thus become useless.

Figure 24:
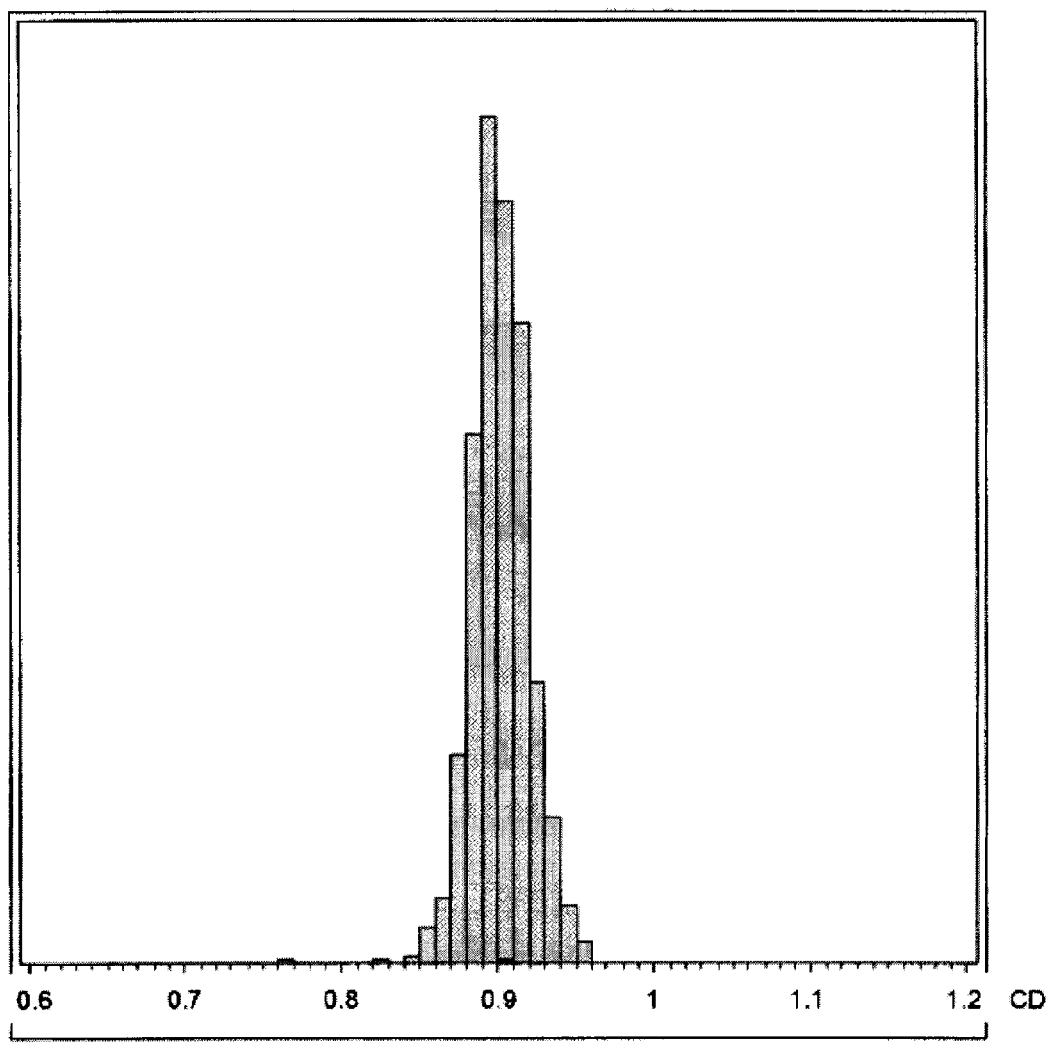
FIG. 24 is a histogram showing the CD value calculated by carrying out the baselayer correction only.

FIG. 24 shows the CD value calculated by carrying out an baselayer correction utilizing the diffracted light L due to low incidence angle by the equations (2), (3), and (4). In FIG. 24, although a correction for the uneven baselayer-influence within the wafer surface (the frying-pan-like turnups) is carried out, the correction regarding each wafer is insufficient. As a result, the average CD value is approximately 0.88, and the standard deviation is approximately 0.022. Although the fluctuation within the wafer surface becomes very small, because offset correction is not made, an overall 12% is shifted (1−0.88=0.12). Therefore, even a normal wafer will be determined as defective in more than half the wafer area.

Figure 25:
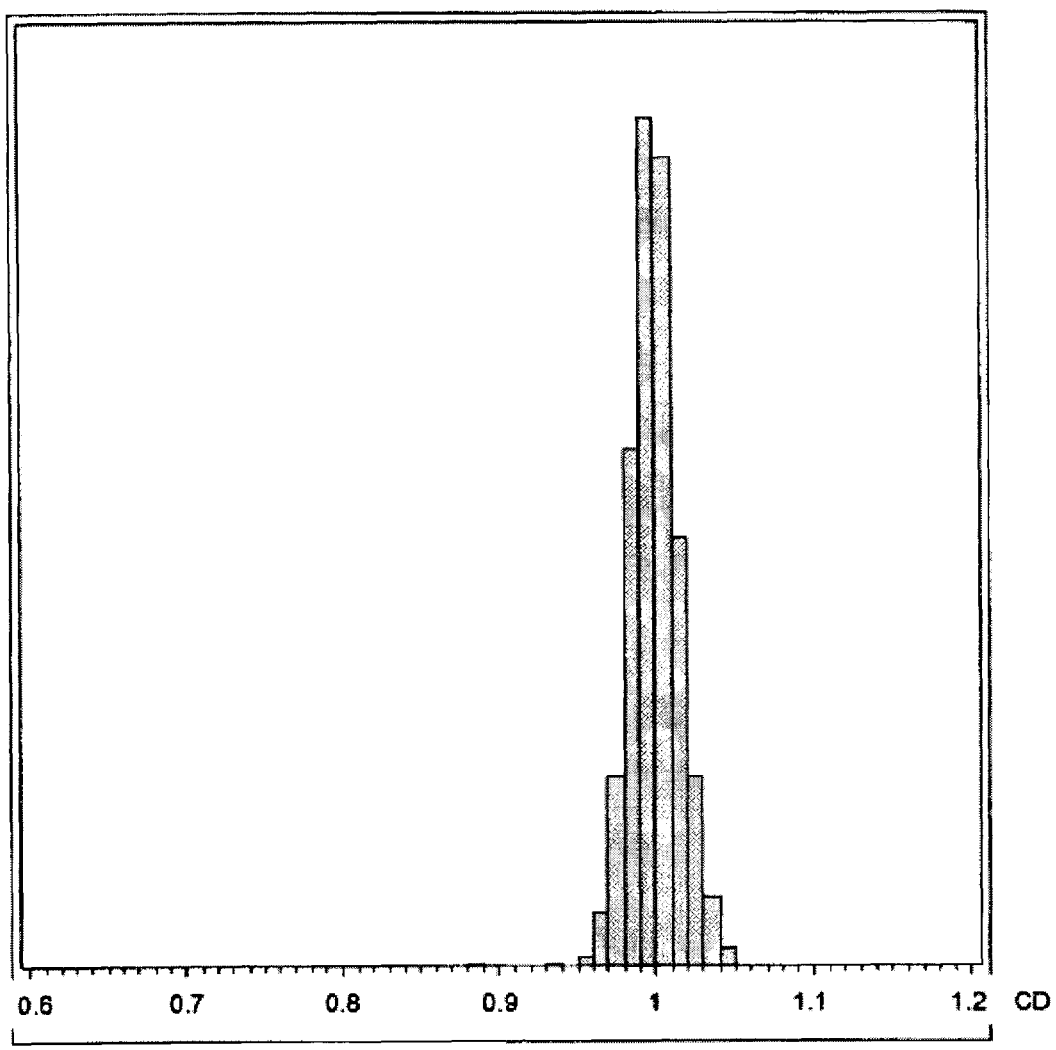
FIG. 25 is a histogram showing the CD value calculated taking into account the base layer correction and the offset correction.

FIG. 25 shows the CD value calculated by carrying out an baselayer correction utilizing all of the baselayer correction techniques in the embodiment, that is, by the equations (2), (3), (4), (5), and (6). In FIG. 25, the correction for the uneven baselayer-influence within the wafer surface (frying-pan-like turnups), and the correction regarding each wafer are carried out. As a result, the average CD value is approximately 1.00, and the standard deviation is approximately 0.020. The commonly utilized 3σ value (three times the standard deviation) is 0.058 (meaning 5.8% with respect to the normalized CD value=1), and thus becomes an appropriately determinable accuracy for the ±10% standard.

In the above manner, according to the embodiment, it is possible to calculate the correct CD value by carrying out a baselayer correction within a wafer surface, and a baselayer correction regarding each wafer. That is, it is possible to correctly detect the surface condition of the wafer 5 even by the diffracted light H due to high incidence angle including the baselayer-influence.

Next, explanations will be made with respect to the principles and algorithm for determining the optimum condition, where a method for determining the optimum condition will also be explained.

Figure 26:
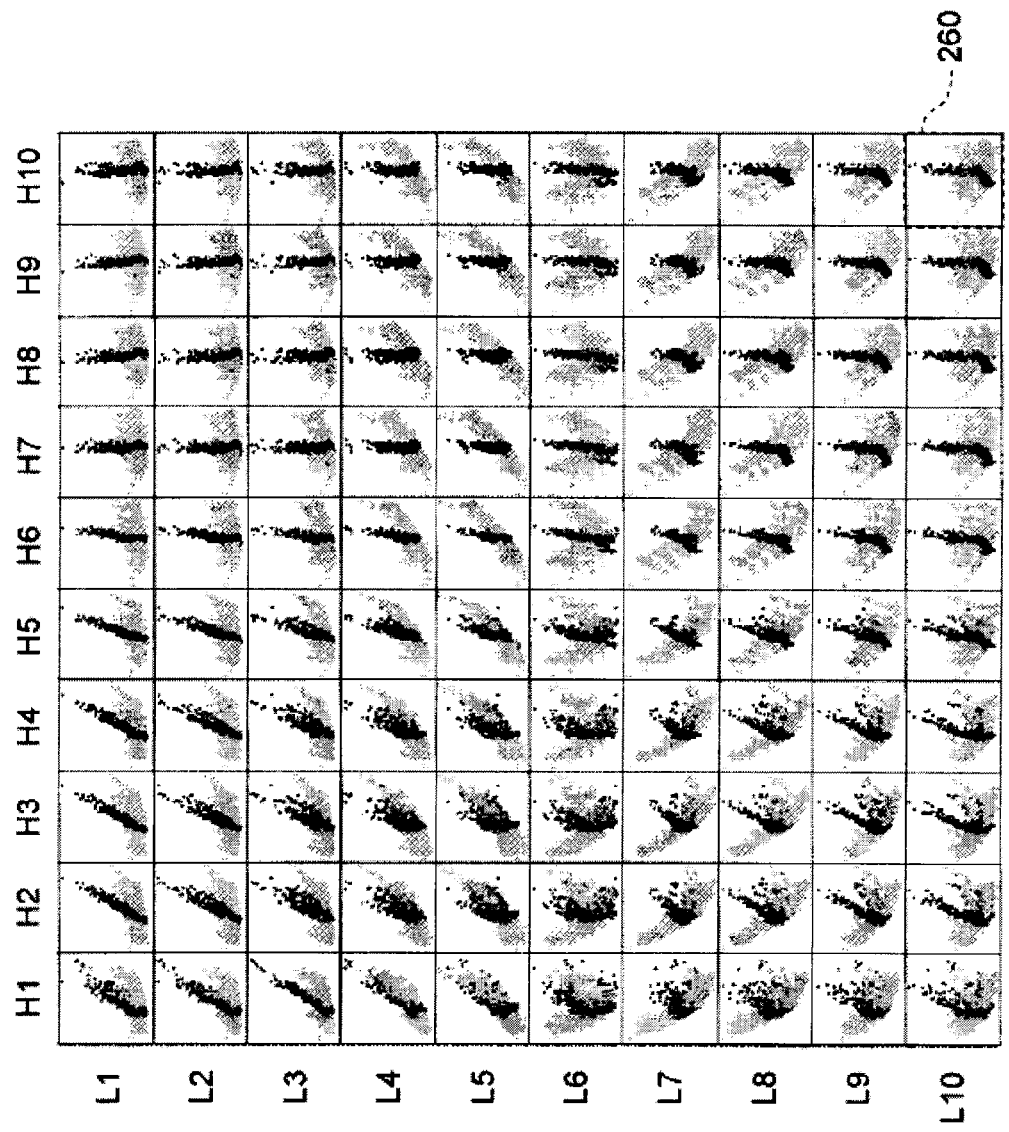
FIG. 26 is a diagram showing an order matrix of the diffracted lights due to the high incidence angle and the diffracted lights due to the low incidence angle with a blue-color wavelength.

In FIG. 26, a relation between the diffracted light H due to high incidence angle and the diffracted light L due to low incidence angle with a blue-color wavelength is shown as a combination according to each of the orders of the diffracted light H due to high incidence angle (the first order to the tenth order), and each of the orders of the diffracted light L due to low incidence angle (the first order to the tenth order), with respect to the reference wafer 100. In the embodiment, FIG. 26 is to be referred to as an order matrix of the diffracted light H due to high incidence angle and the diffracted light L due to low incidence angle.

Each of the graphs (100 in total) in the 10×10 matrix, such as the graph 260 encircled with dashed lines in FIG. 26, takes the diffracted light H due to high incidence angle on the horizontal axis and the diffracted light L due to low incidence angle on the vertical axis, and corresponds to the graph 160 encircled with dashed lines in FIG. 16. Further, since the graph 260 encircled with dashed lines in FIG. 26 is located at the coordinates (H10, L10) in the 10×10 matrix, the horizontal axis represents the tenth-order diffracted light H10 due to high incidence angle, while the vertical axis represents the tenth-order diffracted light L10 due to low incidence angle. Further, the black dots in the 10×10 matrix show the results of the measurement for the shots of standard exposure light amount (64 shots×12 points=768 points), while the gray crosses in the 10×10 matrix show the results of measuring for the shots of high and low exposure light amounts (40 shots× 12 points=480 points in total).

Now, three of the four aforementioned principles will be stated again.

The first principle: The diffracted light H due to high incidence angle is sensitive to the variation in CD value, and includes the baselayer-influence.

The second principle: The diffracted light L due to low incidence angle is insensitive to the variation in CD value, and includes the baselayer-influence.

Figure 27:
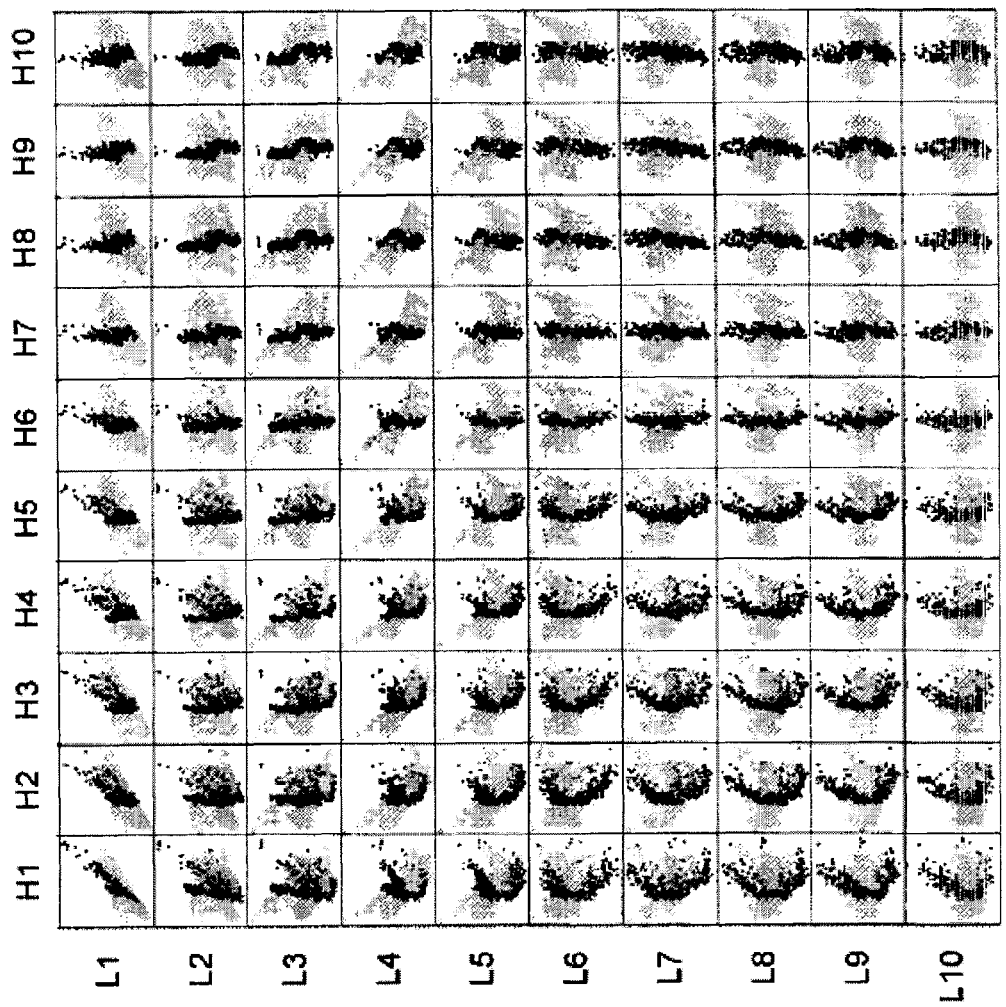
FIG. 27 is a diagram showing an order matrix of the diffracted lights due to the high incidence angle and the diffracted lights due to the low incidence angle with a green-color wavelength.
Figure 28:
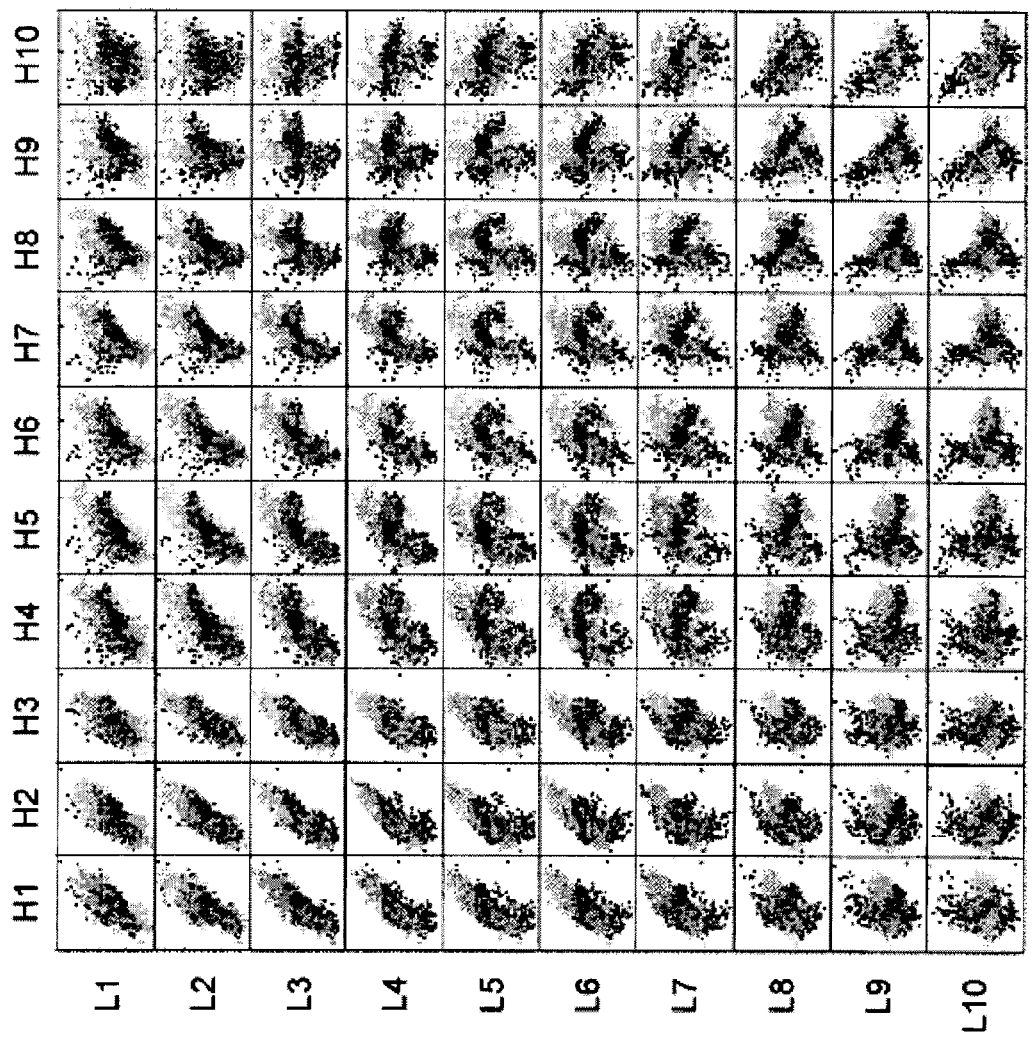
FIG. 28 is a diagram showing an order matrix of the diffracted lights due to the high incidence angle and the diffracted lights due to the low incidence angle with a red-color wavelength.

The third principle: It is possible to eliminate or correct the baselayer-influence under a condition in which the influential inclination from the base layers within the wafer surface for the diffracted light H due to high incidence angle is similar to the influential inclination from the base layers within the wafer surface for the diffracted light L due to low incidence angle These three principles mean that with respect to the graphs in FIG. 26, it is optimum if the following condition is satisfied: (a) the gray crosses distribute horizontally; and (b) the black dots distribute obliquely (positive correlation). With the (a) and (b) as the optimum condition, an comparative examination will be made between FIG. 26 (an order matrix of the diffracted light H due to high incidence angle and the diffracted light L due to low incidence angle with a blue-color wavelength), FIG. 27 (an order matrix of the diffracted light H due to high incidence angle and the diffracted light L due to low incidence angle with a green-color wavelength), and FIG. 28 (an order matrix of the diffracted light H due to high incidence angle and the diffracted light L due to low incidence angle with a red-color wavelength). In FIGS. 27 and 28, there are no combinations of the orders satisfying the optimum condition embodied by (a) and (b).

With respect to FIG. 26 (blue-color wavelength), for example, FIG. 29 shows the case of the seventh-order diffracted light H7 due to high incidence angle, and FIG. 30 shows the case of the seventh-order diffracted light L7 due to low incidence angle. As shown in FIGS. 29 and 30, the seventh-order diffracted light H7 due to high incidence angle is shaped like an upturned straw hat, while the seventh-order diffracted light L7 due to low incidence angle is shaped like a straw hat with an asymmetrical brim. Therefore, they still cannot be regarded as similar to each other, that is, they do not satisfy the third principle described hereinabove. Consequently, it is understood that only the lower-order (the first to fourth orders or so) diffracted lights with the blue-color wavelength among the three wavelengths are possible combinations for satisfying the above first to third principles.

As a specific method for determining the optimum condition, first, it measures multiple points within the surface of the reference wafer 100 with a few different types of wavelengths. Next, it creates an order matrix of the diffracted light H due to high incidence angle and the diffracted light L due to low incidence angle for each wavelength from the measured pupil images. Then, it determines the optimum condition (wavelength and order) to satisfy the first to third principles from the created order matrices.

Further, in the case of the surface inspection device 50 shown in FIG. 5, it is possible to determine the optimum condition for low incidence angles by utilizing the variable deformation aperture stop 63 shown in FIGS. 8A to 9B, and determine the optimum condition (wavelength and order) from the order matrices of the diffracted light H due to high incidence angle and the diffracted light L due to low incidence angle at that time. According to the surface inspection device 50 shown in FIG. 5, incident lights can have high incidence angles and low incidence angles at the same time, and it is possible to separately extract each of the diffracted lights of any orders from the obtained pupil images. Therefore, it is very easy to determine the optimum condition.

The method for determining the optimum condition as described hereinabove is effective for the following cases, that is, the cases of its application to different processes (for example, gate wire and bit contact process, bit line process, and the like), changing the process condition (film thickness and the like), generation change (for example, from the 50 nm generation to the 40 nm generation), and the like. In such cases, because the change in film structure or film thickness leads to the change in baselayer-influence, the process (step) of determining the optimum condition to satisfy the first to fourth principles is carried out before the surface inspection takes place.

Figure 31:
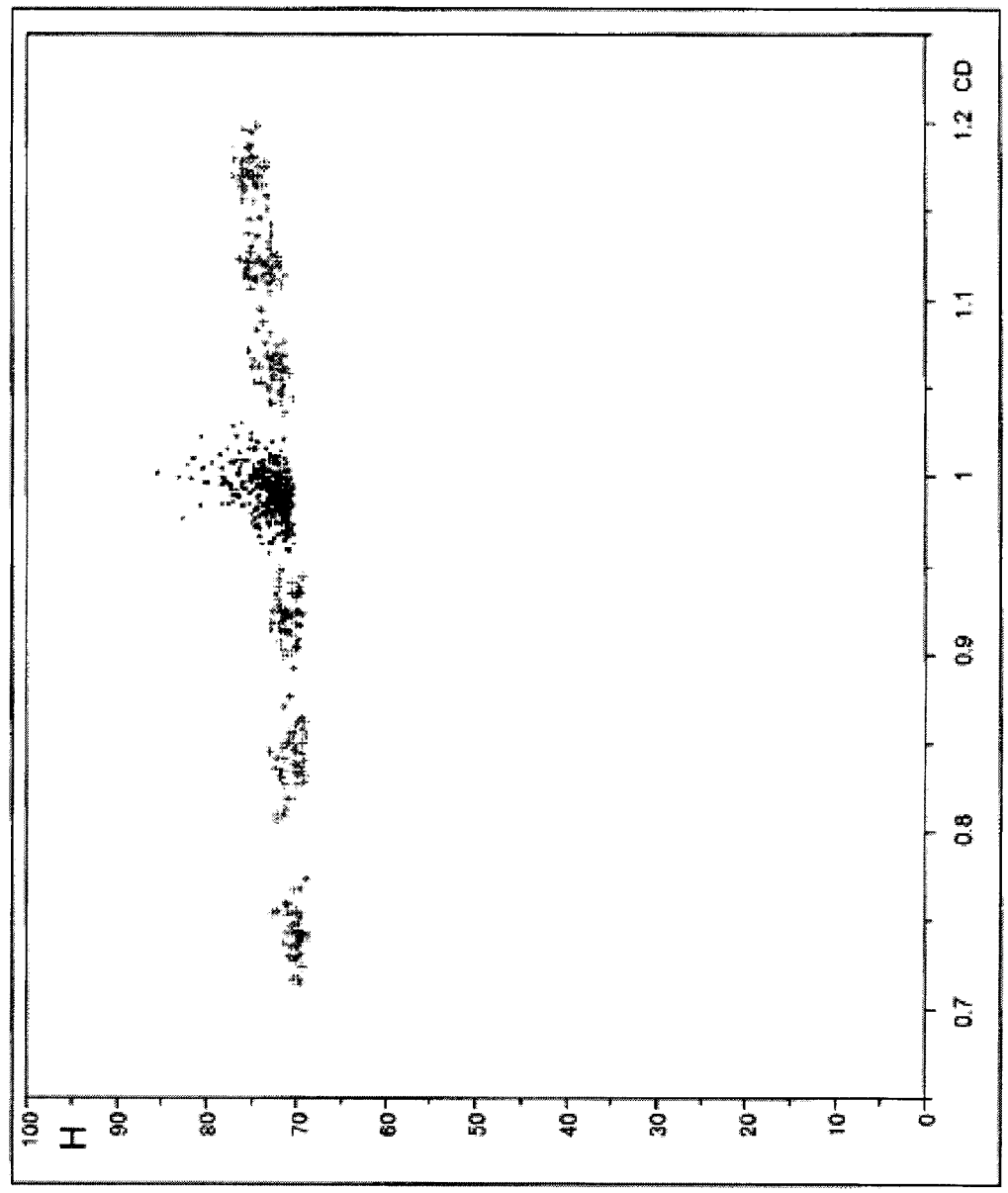
FIG. 31 is a diagram showing a relation between the CD value and the diffracted lights due to the high incidence angle in the case of a P-polarized light incidence.
Figure 32:
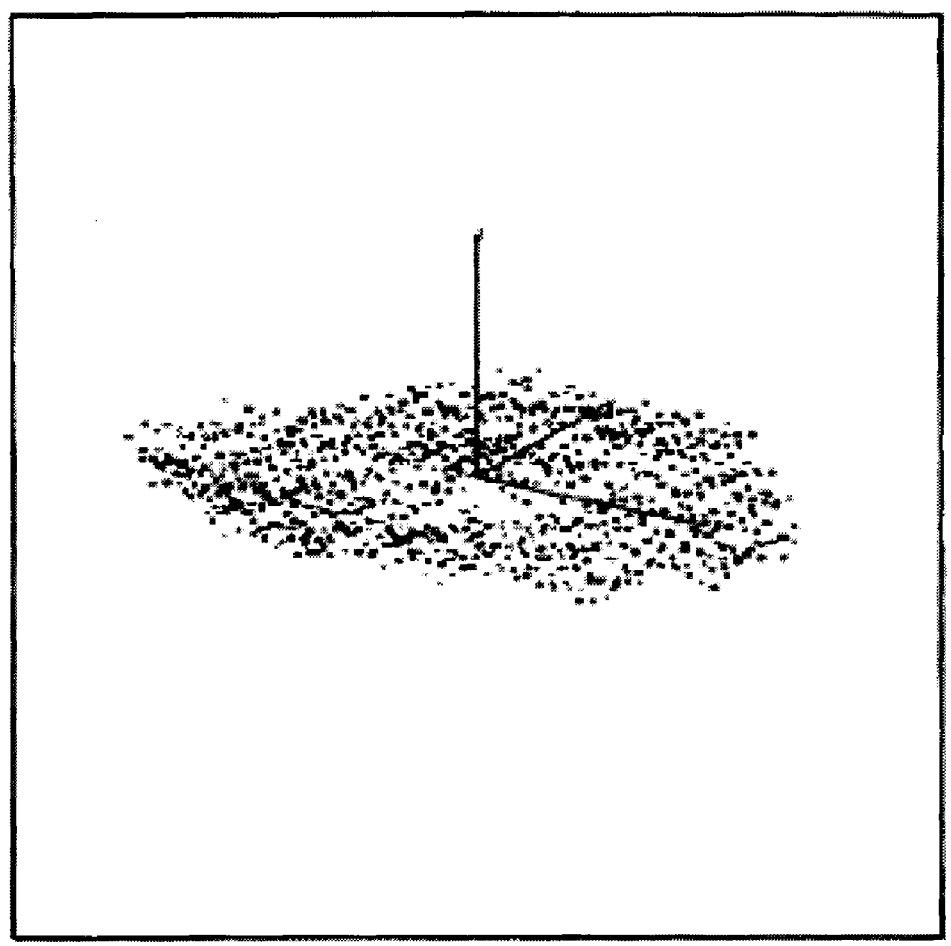
FIG. 32 is a diagram three-dimensionally showing a relation between the X coordinate on the wafer surface and the diffracted lights due to the high incidence angle in the case of the P-polarized light incidence.

Hereinbelow, the optimum polarization will be described. As a result of comparing S-polarized and P-polarized lights, the present inventor has discovered that S-polarized light incidence is more effective than P-polarized light incidence for visible wavelengths having at least a certain degree of wavelength band. FIGS. 31 and 32 show the conditions of P-polarized light incidence with the above light source wavelength. FIG. 31 shows an example of the relation between the CD value change (horizontal axis) and the diffracted light H due to high incidence angle (vertical axis) on the reference wafer 100, and it is understood that the latter is insensitive to the CD value variation. That is, the first principle is not satisfied. FIG. 32 shows a three-dimensional distribution of the diffracted light H due to high incidence angle on the actual wafer 5 with the same incidence angle, polarization, and diffraction order as those of FIG. 31. As is understood from FIG. 32, the distribution is asymmetric (potato-chip-like distribution; one side slopes upward but the other side slopes downward), and thereby different from the frying-pan-like distribution capable of achieving a high accuracy of calculating the CD value. For these reasons, P-polarized lights can be regarded as inferior to S-polarized lights.

Further, in the aforementioned offset correction, as shown in the equations (5) and (6), the average value of measuring the central shot on the measuring wafer 5 is corrected by the difference from the average value of measuring the central shot 107 on the reference wafer 100. This is based on the premise that the central shot is non-defective in terms of the CD value. However, the central shot may as well be defective. Therefore, by default, a comparison is carried out for the central shot. In the case of a defective central shot (a shot including defects such as defocus and the like, for example), it is preferable to compare the average measurement values between the shots within a non-defective region different from that of the central shot. For this purpose, for example, an automatic macroscopic inspection device 35 (shown in FIG. 1 with long dashed double-dotted lines) may be connected with the surface inspection device 1 of the embodiment so as to communicate with each other, and the result (the information including the places of non-defective shots and the places of defective shots) obtained by the automatic macroscopic inspection device 35 with a high throughput is utilized after being inputted to the computation processing section 30 or the like.

A detailed illustration of the automatic macroscopic inspection device 35 is omitted. The automatic macroscopic inspection device 35 is configured to carry out defect detection by irradiating light on a semiconductor wafer, receiving the diffracted lights from the repetition pattern on the wafer, and detecting the change of the diffracted light amount from the portion of a different CD value or pattern profile, and is widely utilized in semiconductor plants. Because it is possible for the automatic macroscopic inspection device 35 of this kind to irradiate light on the entire wafer surface at one time, it is possible to detect defective places at a high speed, and output the defective places in terms of the wafer coordinates to the outside. Therefore, if the automatic macroscopic inspection device 35 has not detected any defects, or if it has detected some detects with wafer coordinates not belonging to the central shot, then by default as it is, a comparison is made between the central shot of the measuring wafer 5 and the central shot of the reference wafer 100. On the other hand, if the automatic macroscopic inspection device 35 has detected some defects with the wafer coordinates belonging to the central shot, then it is preferable to take a non-defective place in the vicinity of the center as the shot for the comparison with the reference wafer 100.

On the other hand, with respect to conventional surface inspection devices, there was a method for restricting as much as possible the incident light from transmission down to the base layers by utilizing a DUV (deep ultraviolet) wavelength. However, a DUV light source had some negative aspects. For example, it had a short life but a high price; it needed a chemical clean technique; etc. Further, since the baselayer-influence was not actively corrected or eliminated in the method, it was not possible to meet the demands of a quantitative performance such as the CD value calculation and the like.

In contrast, according to the embodiment, because it is possible to correct or eliminate the baselayer-influence even for visible lights, a quantitative performance is available along with a low cost, a long life and a simplified in-device process and, furthermore, a high-speed inspection is possible in comparison with the time consuming measurements by such as a conventional CD-SEM (about five seconds of time is needed for one point). Further, since the visual field can cover a range of hundreds of micrometers, there is an unparalleled advantage in that it is possible to attain the CD value distribution within a shot and inspect the entire surface of the wafer 5 without carrying out one-point measurement such as done by a CD-SEM.

Further, in the embodiment described hereinabove, the offset correction is made by measuring the central shot on the reference wafer 100. However, the offset correction is not limited to this method but may be made by utilizing the CD value measured by a CD-SEM 36 (shown in FIG. 1 with long dashed double-dotted lines) to compare the same with the CD value calculated in the embodiment for the same place so as to equalize the both. For example, if the CD-SEM 36 measures nine points within the central shot of the wafer 5 and the average value is supposed to be SEM9, then the corresponding CD value calculated in the embodiment for the same shot should be SEM9=CD12 when the average value is supposed to be CD12 for 12 points within the shot. For example, if SEM9=100 nm and CD12=110 nm, it is possible to treat the results of subtracting 10 nm from all corresponding CD values as the absolute CD values.

Further, in a CD-SEM, the measurement is made by irradiating an electron beam on an extremely narrow region (a few micrometers), while in the embodiment, a visual field of tens to hundreds of micrometers is optically measured; hence, there is a fundamental difference therebetween. Therefore, it is possible to reduce the correction error through averaging. This is the reason of utilizing the average value.

What is claimed is:

1. A surface inspection device comprising:
an illumination section which irradiates illumination lights on a surface of a semiconductor substrate having a plurality of layers;
a detection section which detects diffracted lights from the surface of the semiconductor substrate on which the illumination lights are irradiated; and
an inspection section which detects a change of a condition of a pattern on the surface of the semiconductor substrate based on information of the diffracted lights detected by the detection section,
wherein the illumination section irradiates, on the surface of the semiconductor substrate, a first illumination light which falls on the surface of the semiconductor substrate at a first incidence angle with respect to a normal of the semiconductor substrate, and a second illumination light which falls on the surface of the semiconductor substrate at a second incidence angle different from the first incidence angle with respect to the normal of the semiconductor substrate;
the detection section detects a first diffracted light caused by the first illumination light irradiated on the surface of the semiconductor substrate, and a second diffracted light caused by the second illumination light irradiated on the surface of the semiconductor substrate; and
the inspection section detects the change of the condition of the pattern on the surface to which a correction is made for an influence from layers other than the uppermost layer, based on information of the first diffracted light and the second diffracted light detected by the detection section.

2. The surface inspection device according to claim 1, wherein the second incidence angle is smaller than the first incidence angle, and the inspection section detects the change of the condition of the pattern on the surface to which the correction is made for the influence on the first diffracted light due to the first incidence angle from the layers other than the uppermost layer based on the second diffracted light due to the second incidence angle.

3. The surface inspection device according to claim 1, wherein the illumination section has a polarization portion, and the first illumination light and the second illumination light include an S-polarized component with respect to the surface of the semiconductor substrate.

4. The surface inspection device according to claim 1, wherein the inspection section utilizes information of the first diffracted light and the second diffracted light obtained by irradiating the first illumination light and the second illumination light respectively on a surface of a reference substrate with a known amount of change in surface condition, so as to find an amount of the change of the condition of the pattern on the surface to which the correction is made for the influence from the layers other than the uppermost layer.

5. A inspection device comprising:
a illumination section which is configured to illuminate a spot on an object by a plurality of light fluxes of which incident angles are different from each other;
an objective lens into which a reflected light from the irradiated object enters; and
a detecting section which detect a luminance of the reflected light on a pupil plane or a plane conjugate to the pupil plane of the objective lens.

6. The inspection device according to claim 5, wherein the illumination section includes an aperture stop which is located at an eccentric position from an optical axis.

7. The inspection device according to claim 5, wherein the illumination section includes a aperture stop in which a plurality of apertures corresponding to the light fluxes respectively is formed.

8. The inspection device according to claim 5, wherein the illumination section includes a plurality of lens of which numerical aperture is different from each other and which are configured to be removably inserted in the optical axis of the illumination.

9. The inspection device according to claim 5, wherein the illumination section illuminates the object with a predetermined polarization state.

10. The inspection device according to claim 5, wherein the illumination section is configured to illuminate by illumination lights having a plurality of wavelengths.

11. The inspection device according to claim 5, further comprising a supporting section which supports the object so that the object is rotatable around an optical axis of the objective lens.

12. A surface inspection method for detecting a change of a condition of a pattern on a surface of a semiconductor substrate based on information of detected diffracted lights by irradiating illumination lights on the surface of the semiconductor substrate having a plurality of layers and detecting the diffracted lights from the surface of the semiconductor substrate on which the illumination lights are irradiated, the method comprising:
irradiating, on the surface of the semiconductor substrate, a first illumination light to fall on the surface of the semiconductor substrate at a first incidence angle with respect to a normal of the semiconductor substrate, and a second illumination light to fall on the surface of the semiconductor substrate at a second incidence angle different from the first incidence angle with respect to the normal of the semiconductor substrate;
detecting a first diffracted light caused by the first illumination light irradiated on the surface of the semiconductor substrate, and a second diffracted light caused by the second illumination light irradiated on the surface of the semiconductor substrate; and
detecting the change of the condition of the pattern on the surface to which a correction is made for an influence from layers other than the uppermost layer, based on information of the detected first diffracted light and the detected second diffracted light.

13. The surface inspection method according to claim 12, wherein the second incidence angle is smaller than the first incidence angle, and upon detecting the change of the condition of the pattern on the surface, the change of the condition of the pattern on the surface to which the correction is made for the influence on the first diffracted light due to the first incidence angle from the layers other than the uppermost layer is detected based on the second diffracted light due to the second incidence angle.

14. The surface inspection method according to claim 12, wherein upon irradiating the first and second illumination lights, the first illumination light and the second illumination light are lights including an S-polarized component with respect to the surface of the semiconductor substrate.

15. The surface inspection method according to claim 12, wherein upon detecting the change of the condition of the pattern on the surface, an amount of the change of the condition of the pattern on the surface to which the correction is made for the influence from the layers other than the uppermost layer is obtained by information of the first diffracted light and the second diffracted light obtained by irradiating the first illumination light and the second illumination light respectively on a surface of a reference substrate with a known amount of change in surface condition.

16. The surface inspection method according to claim 15, wherein upon detecting the change of the condition of the pattern on the surface, the amount of the change of the condition of the pattern on the surface to which the correction is made for the influence from the layers other than the uppermost layer is obtained by the information of the first diffracted light and the second diffracted light arising from the surface of the reference substrate, and the information of the first diffracted light and the second diffracted light arising from the vicinity of the surface center of the semiconductor substrate.

17. The surface inspection method according to claim 15, wherein upon detecting the change of the condition of the pattern on the surface, the amount of the change of the condition of the pattern on the surface to which the correction is made for the influence from the layers other than the uppermost layer is obtained by the information of the first diffracted light and the second diffracted light arising from the surface of the reference substrate, and the information of the first diffracted light and the second diffracted light arising from a normal portion of the semiconductor substrate predetermined as normal by a defect inspection device which is configured to collectively inspect an entire surface of the semiconductor substrate.

18. The surface inspection method according to claim 15, wherein upon detecting the change of the condition of the pattern on the surface, the amount of the change of the condition of the pattern on the surface to which the correction is made for the influence from the layers other than the uppermost layer is obtained by a surface condition of the semiconductor substrate measured in advance by an electron microscope device which is configured to partially measure the surface condition.

19. The surface inspection method according to claim 12, further comprising determining: diffraction orders of the first diffracted light and the second diffracted light utilized upon detecting the change of the condition of the pattern on the surface; wavelengths of the first illumination light and the second illumination light irradiated upon irradiating the first and second illumination lights; and the second incidence angle, before irradiating the first and second illumination lights, detecting the first and second diffracted lights, and detecting the change of the condition of the pattern on the surface.

20. The surface inspection method according to claim 12, wherein the first illumination light and the second illumination light have wavelengths within the range of visible lights.

21. The surface inspection method according to claim 12, wherein upon detecting the first and second diffracted lights, the first diffracted light and the second diffracted light are detected on a pupil plane or a plane conjugate to the pupil plane in an optical system.

* * * * *